(12) United States Patent
Kottenstette et al.

(10) Patent No.: US 11,639,847 B2
(45) Date of Patent: *May 2, 2023

(54) SYSTEM AND METHOD FOR DETECTING A POSITION OF A GUIDE CATHETER SUPPORT

(71) Applicant: Corindus, Inc., Waltham, MA (US)

(72) Inventors: Nicholas Kottenstette, Worcester, MA (US); Peter Falb, Waltham, MA (US); Timothy Deignan, Belmont, MA (US); Per Bergman, West Roxbury, MA (US)

(73) Assignee: Corindus, Inc., Newton, MA (US)

( * ) Notice: Subject to any disclaimer, the term of this patent is extended or adjusted under 35 U.S.C. 154(b) by 303 days.

This patent is subject to a terminal disclaimer.

(21) Appl. No.: 17/247,759

(22) Filed: Dec. 22, 2020

(65) Prior Publication Data

US 2021/0108910 A1    Apr. 15, 2021

Related U.S. Application Data

(63) Continuation of application No. 15/739,031, filed as application No. PCT/US2016/040262 on Jun. 30, 2016, now Pat. No. 10,900,771.

(Continued)

(51) Int. Cl.
*G01B 11/14* (2006.01)
*A61B 34/30* (2016.01)
(Continued)

(52) U.S. Cl.
CPC .......... *G01B 11/14* (2013.01); *A61B 5/1076* (2013.01); *A61B 34/20* (2016.02); *A61B 34/30* (2016.02);
(Continued)

(58) Field of Classification Search
CPC ........ A61B 2034/2055; G01B 2210/30; G01B 11/00–005; G01B 11/14
See application file for complete search history.

(56) References Cited

U.S. PATENT DOCUMENTS

| 4,593,967 A | 6/1986 | Haugen |
|---|---|---|
| 5,029,304 A | 7/1991 | Tolmie, Jr. |

(Continued)

FOREIGN PATENT DOCUMENTS

| JP | 2010506621 | 3/2010 |
|---|---|---|
| JP | 2018519087 | 7/2018 |

(Continued)

OTHER PUBLICATIONS

Extended Search Report for Application No. 20154304.8, dated Feb. 8, 2021.

(Continued)

*Primary Examiner* — Dominic J Bologna
*Assistant Examiner* — Amanda Merlino

(57) ABSTRACT

A catheter procedure system includes a base and a robotic mechanism having a longitudinal axis and being movable relative to the base along the longitudinal axis. The robotic mechanism includes a robotic drive base including at least one drive mechanism, a cassette operatively secured to the robotic drive base, a rigid guide coupled to the cassette and fixed relative to the robotic mechanism and a flexible track having a distal end, a proximal end and a plurality of reflective sections. At least a portion of the flexible track is disposed within the rigid guide. The robotic mechanism also includes a position detector mounted to the robotic drive base and positioned beneath the flexible track. The position detector is configured to detect light reflected off of the (Continued)

reflective sections of the flexible track and to determine the position of the distal end of the flexible track based on the detected reflected light.

20 Claims, 16 Drawing Sheets

Related U.S. Application Data

(60) Provisional application No. 62/186,832, filed on Jun. 30, 2015.

(51) Int. Cl.
| | | |
|---|---|---|
| G01B 11/00 | (2006.01) | |
| A61B 34/20 | (2016.01) | |
| A61B 34/37 | (2016.01) | |
| A61B 5/107 | (2006.01) | |
| A61B 17/00 | (2006.01) | |
| A61B 90/00 | (2016.01) | |
| A61B 5/00 | (2006.01) | |
| A61B 6/00 | (2006.01) | |
| A61F 2/958 | (2013.01) | |
| A61M 39/10 | (2006.01) | |

(52) U.S. Cl.
CPC ............ *A61B 34/37* (2016.02); *G01B 11/002* (2013.01); *A61B 5/0036* (2018.08); *A61B 6/503* (2013.01); *A61B 2017/00477* (2013.01); *A61B 2034/2055* (2016.02); *A61B 2034/2059* (2016.02); *A61B 2034/301* (2016.02); *A61B 2090/061* (2016.02); *A61F 2/958* (2013.01); *A61M 39/105* (2013.01)

(56) References Cited

U.S. PATENT DOCUMENTS

| | | |
|---|---|---|
| 5,427,107 A | 6/1995 | Milo et al. |
| 5,437,290 A | 8/1995 | Bolger et al. |
| 6,167,607 B1 | 1/2001 | Pryor |
| 2002/0165537 A1 | 11/2002 | Kelley et al. |
| 2003/0187369 A1 | 10/2003 | Lewis et al. |
| 2007/0191825 A1 | 8/2007 | Cronin et al. |
| 2007/0235272 A1 | 10/2007 | Sieh et al. |
| 2008/0146942 A1 | 6/2008 | Dala-Krishna |
| 2009/0141263 A1 | 6/2009 | Cronin et al. |
| 2009/0318799 A1 | 12/2009 | Wurmfeld et al. |
| 2011/0096331 A1 | 4/2011 | Jung et al. |
| 2012/0071856 A1 | 3/2012 | Goldfarb et al. |
| 2012/0179167 A1 | 7/2012 | Wenderow et al. |
| 2012/0184955 A1 | 7/2012 | Pivotto et al. |

FOREIGN PATENT DOCUMENTS

| | | |
|---|---|---|
| WO | 2007098494 | 8/2007 |
| WO | 2009092059 | 7/2009 |
| WO | 2009120944 | 10/2009 |
| WO | 2009137410 | 11/2009 |
| WO | 2015057821 A1 | 4/2015 |

OTHER PUBLICATIONS

Extended European Search Report for EP 16818744.1; dated Dec. 18, 2018; 8 pages.
International Search Report and Written Opinion for PCT/US2016/040262; dated Sep. 22, 2016; 8 pages.

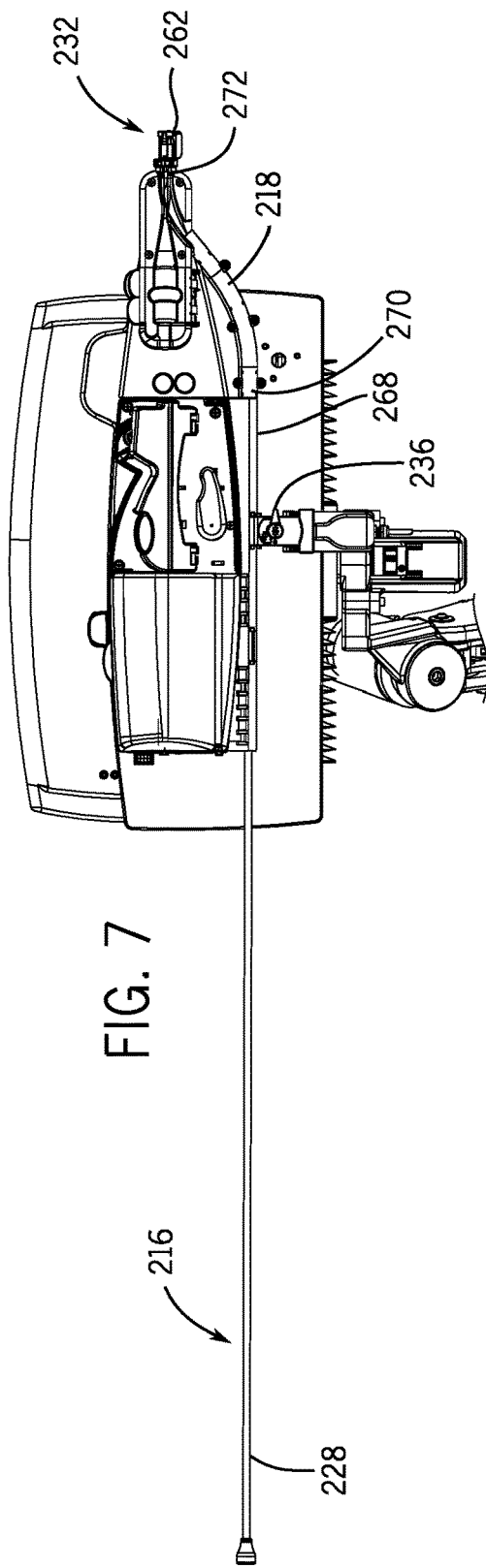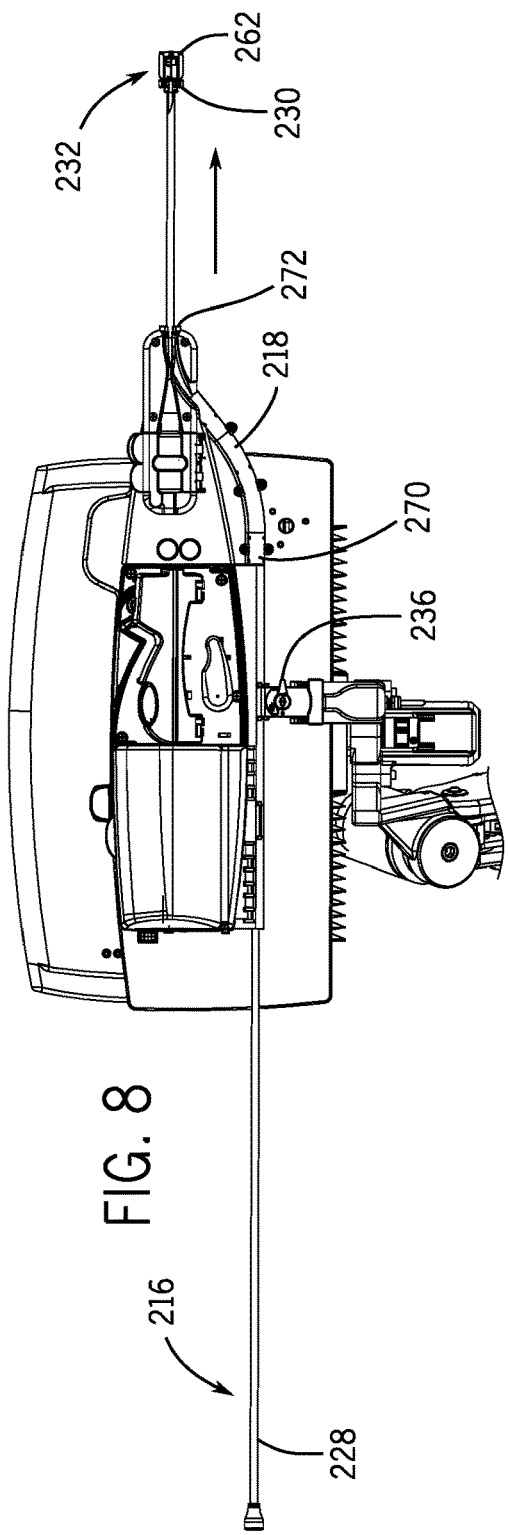

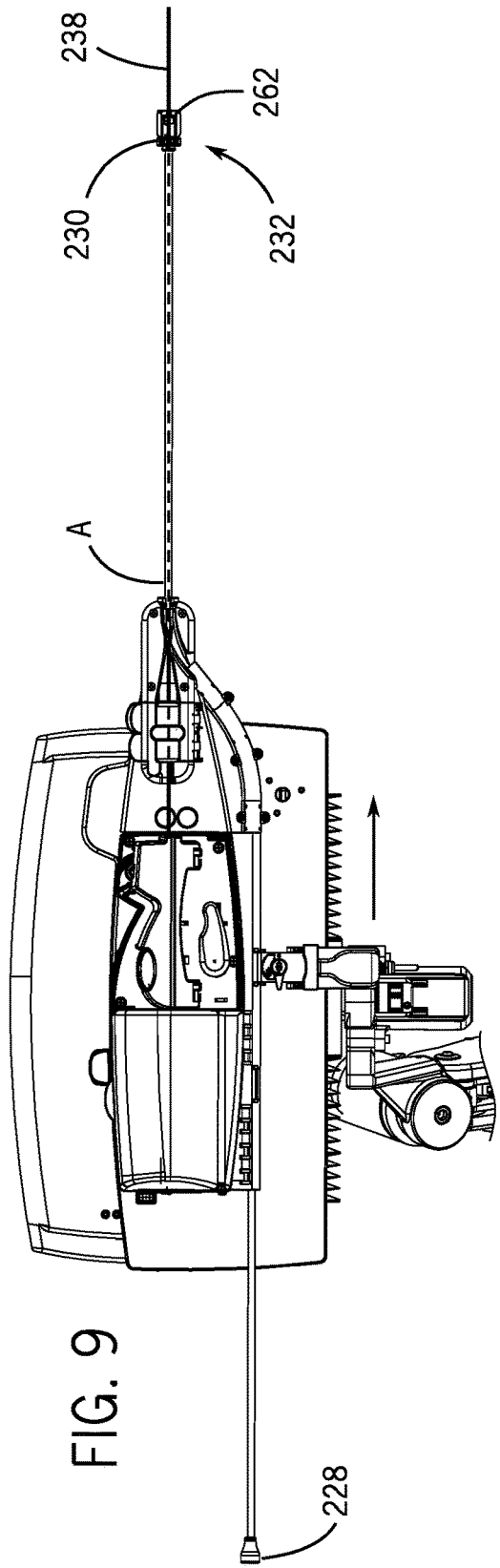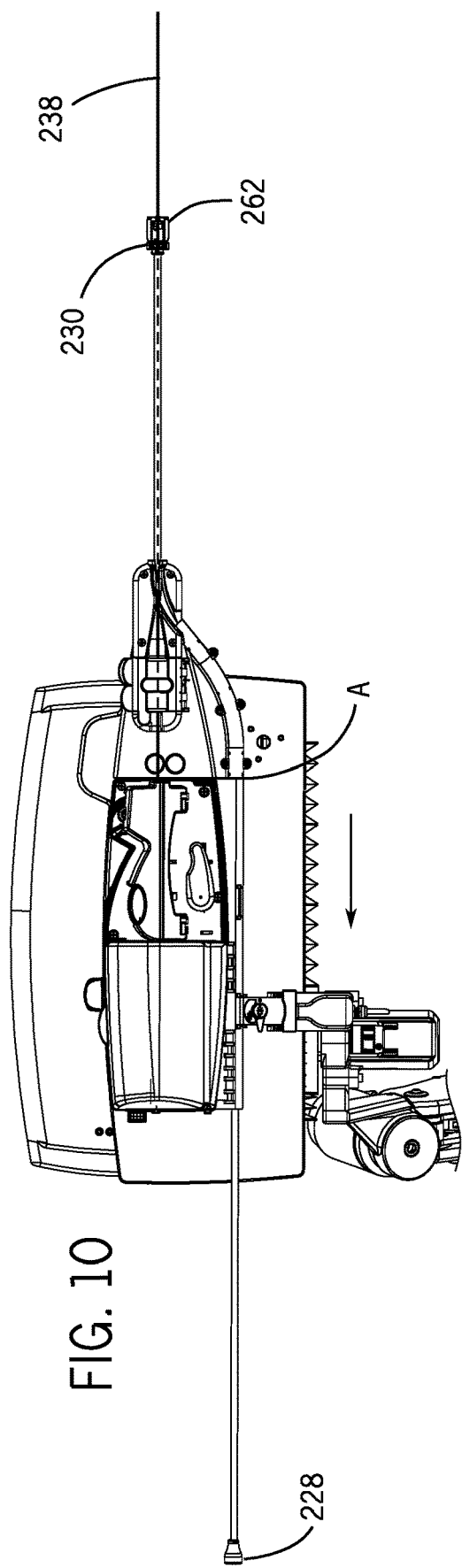

SYSTEM AND METHOD FOR DETECTING A POSITION OF A GUIDE CATHETER SUPPORT

CROSS REFERENCE TO RELATED APPLICATIONS

The present application is a continuation of U.S. application Ser. No. 15/739,031, filed Dec. 21, 2017, entitled SYSTEM AND METHOD FOR DETECTING A POSITION OF A GUIDE CATHETER SUPPORT, which is a 371 National Stage Entry of PCT/US2016/040262, filed Jun. 30, 2016, entitled SYSTEM AND METHOD FOR DETECTING A POSITION OF A GUIDE CATHETER SUPPORT, which claims the benefit of U.S. Provisional Application No. 62/186,832, filed Jun. 30, 2015, entitled ABSOLUTE LINEAR POSITION SENSING WITH PHOTO DIODES, herein incorporated by reference in their entireties.

FIELD OF THE INVENTION

The present invention relates generally to the field of robotic catheter systems for performing diagnostic and/or therapeutic procedures and in particular, to an apparatus and method for detecting a position of a guide catheter support.

BACKGROUND OF THE INVENTION

Catheters may be used for many medical procedures, including inserting a guide wire, delivering a stent and delivering and inflating a balloon. Catheterization procedures are commonly performed for diagnosis and treatment of diseases of the heart and vascular systems. The catheterization procedure is generally initiated by inserting a guide wire into a blood vessel in the patient's body. The guide wire is then guided to the desired location, most commonly in one of the heart vessels or elsewhere in the vascular system. At this point, the catheter is slid over the guide wire into the blood vessel and/or heart. In some procedures, the catheter is equipped with a balloon or stent that when deployed at the site of the lesion allows for increased blood flow through the portion of the coronary artery that is affected by the lesion.

For manual insertion of a catheter, the physician applies torque and axial push force on the proximal end of a guide wire to effect tip direction and axial advancement at the distal end. Robotic catheter system have been developed that may be used to aid a physician in performing a catheterization procedure such as a percutaneous coronary intervention (PCI). The physician uses a robotic catheter system to precisely steer a coronary guide wire, balloon catheter or stent delivery system in order to, for example, widen an obstructed artery. In order to perform PCI, the various elongated medical devices (e.g., guide wire, guide catheter, working catheter) must be navigated through the coronary anatomy to a target lesion. While observing the coronary anatomy using fluoroscopy, the physician manipulates the elongated medical device into the appropriate vessels toward the lesion and avoid advancing into side branches. A robotic catheter procedure system includes drive mechanisms to drive various elongated medical devices (e.g., guide wire, guide catheter, working catheter) used in catheterization procedures to provide linear and rotational movement of the elongated medical device.

During one type of intervention procedure, a guide catheter is inserted into either a patient's femoral or radial artery through an introducer and the guide catheter is positioned proximate the coronary ostium of a patient's heart. During the procedure, the guide catheter is used to guide other elongated medical devices such as a guide wire and balloon catheter into a patient. If during a PCI procedure the guide catheter begins to slip out of the ostium, an operator may wish to relocate the end of the guide catheter robotically. A guide catheter support structure, such as a flexible track, may be used to provide support to the guide catheter while it is moved.

It would be desirable to provide a system and method for detecting a position of a guide catheter support.

BRIEF DESCRIPTION OF THE INVENTION

In accordance with an embodiment, a catheter procedure system includes a base and a robotic mechanism having a longitudinal axis and being movable relative to the base along the longitudinal axis, the robotic mechanism includes a robotic drive base including at least one drive mechanism, a cassette operatively secured to the robotic drive base, a rigid guide coupled to the cassette and fixed relative to the robotic mechanism, a flexible track having a distal end, a proximal end and a plurality of reflective sections, wherein at least a portion of the flexible track is disposed within the rigid guide and a position detector mounted to the robotic drive base and positioned beneath the flexible track, the position detector configured detect light reflected off of the reflective sections of the flexible track and to determine the position of the distal end of the flexible track based on the detected reflected light.

BRIEF DESCRIPTION OF THE DRAWINGS

The invention will become more fully understood from the following detailed description, taken in conjunction with the accompanying drawings, wherein the reference numerals refer to like parts in which:

FIG. 7 is a top plan view of the catheter procedure system with the flexible track in the fully retracted position in accordance with an embodiment;

FIG. 8 is a top plan view of the catheter procedure system with the flexible track in an extended position in accordance with an embodiment;

FIG. 9 is a top plan view of the catheter procedure system with the robotic mechanism in a first position in accordance with an embodiment;

FIG. 10 is a top plan view of the catheter procedure system with the robotic mechanism in a second extended position in accordance with an embodiment;

DETAILED DESCRIPTION

Figure 1:
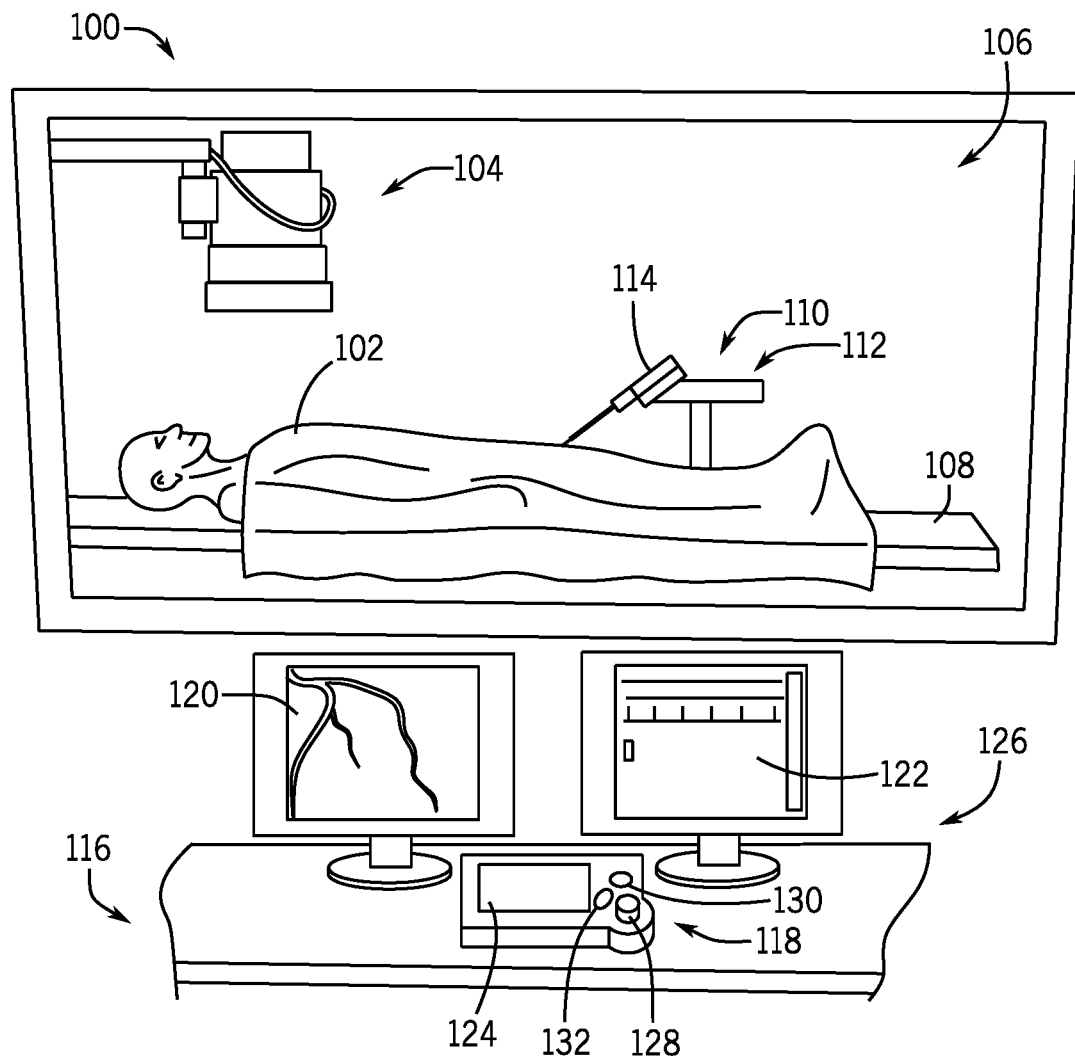
FIG. 1 is a perspective view of an exemplary catheter procedure system in accordance with an embodiment.

FIG. 1 is a perspective view of an exemplary catheter procedure system in accordance with an embodiment. In FIG. 1, a catheter procedure system 100 may be used to perform catheter based medical procedures (e.g., a percutaneous intervention procedure). Catheter based medical procedures may include diagnostic catheterization procedures during which one or more catheters are used to aid in the diagnosis of a patient's disease. For example, during one embodiment of a catheter based diagnostic procedure, a contrast media is injected onto one or more coronary arteries through a catheter and an image of the patient's heart is taken. Catheter based medical procedures may also include catheter based therapeutic procedures (e.g., angioplasty, stent placement, treatment of peripheral vascular disease, etc.) during which a catheter is used to treat a disease. It should be noted, however, that one skilled in the art would recognize that certain specific percutaneous intervention devices or components (e.g., type of guide wire, type of catheter, etc.) will be selected based on the type of procedure that is to be performed. Catheter procedure system 100 is capable of performing any number of catheter based medical procedures with minor adjustments to accommodate the specific percutaneous intervention devices to be used in the procedure. In particular, while the embodiments of catheter procedure system 100 describe herein are explained primarily in relation to the diagnosis and/or treatment of coronary disease, catheter procedure system 100 may be used to diagnose and/or treat any type of disease or condition amenable to diagnosis and/or treatment via a catheter based procedure.

Catheter procedure system 100 includes lab unit 106 and workstation 116. Catheter procedure system 100 includes a robotic catheter system, shown as bedside system 110, located within lab unit 106 adjacent a patient 102. Patient 102 is supported on a table 108. Generally, bedside system 110 may be equipped with the appropriate percutaneous intervention devices or other components (e.g., guide wires, guide catheters, working catheters such as balloon catheters and stent delivery system, contrast media, medicine, diagnostic catheters, etc.) to allow the user to perform a catheter based medical procedure via a robotic system by operating various controls such as the controls located at workstation 116. Bedside system 110 may include any number and/or combination of components to provide bedside system 110 with the functionality described herein. Bedside system 110 includes, among other elements, a cassette 114 supported by a robotic arm 112 which is used to automatically feed a guide wire into a guide catheter seated in an artery of the patient 102.

Bedside system 110 is in communication with workstation 116, allowing signals generated by the user inputs of workstation 116 to be transmitted to bedside system 110 to control the various functions of bedside system 110. Bedside system 110 may also provide feedback signals (e.g., operating conditions, warning signals, error codes, etc.) to workstation 116. Bedside system 110 may be connected to workstation 116 via a communication link 140 (shown in FIG. 4) that may be a wireless connection, cable connections, or any other means capable of allowing communication to occur between workstation 116 and bedside system 110.

Workstation 116 includes a user interface 126 configured to receive user inputs to operate various components or systems of catheter procedure system 100. User interface 126 includes controls 118 that allow the user to control bedside system 110 to perform a catheter based medical procedure. For example, controls 118 may be configured to cause bedside system 110 to perform various tasks using the various percutaneous intervention devices with which bedside system 110 may be equipped (e.g., to advance, retract, or rotate a guide wire, advance, retract or rotate a working catheter, advance, retract, or rotate a guide catheter, inflate or deflate a balloon located on a catheter, position and/or deploy a stent, inject contrast media into a catheter, inject medicine into a catheter, or to perform any other function that may be performed as part of a catheter based medical procedure). Cassette 114 includes various drive mechanisms to cause movement (e.g., axial and rotational movement) of the components of the bedside system 110 including the percutaneous intervention devices.

In one embodiment, controls 118 include a touch screen 124, one or more joysticks 128 and buttons 130, 132. The joystick 128 may be configured to advance, retract, or rotate various components and percutaneous intervention devices such as, for example, a guide wire, a guide catheter or a working catheter. Buttons 130, 132 may include, for example, an emergency stop button and a multiplier button. When an emergency stop button is pushed a relay is triggered to cut the power supply to bedside system 110. Multiplier button acts to increase or decrease the speed at which the associated component is moved in response to a manipulation of controls 118. In one embodiment, controls 118 may include one or more controls or icons (not shown) displayed on touch screen 124, that, when activated, causes operation of a component of the catheter procedure system 100. Controls 118 may also include a balloon or stent control that is configured to inflate or deflate a balloon and/or a stent. Each of the controls may include one or more buttons, joysticks, touch screen, etc. that may be desirable to control the particular component to which the control is dedicated. In addition, touch screen 124 may display one or more icons (not shown) related to various portions of controls 118 or to various components of catheter procedure system 100.

User interface 126 may include a first monitor or display 120 and a second monitor or display 122. First monitor 120 and second monitor 122 may be configured to display information or patient specific data to the user located at workstation 116. For example, first monitor 120 and second monitor 122 may be configured to display image data (e.g., x-ray images, MRI images, CT images, ultrasound images, etc.), hemodynamic data (e.g., blood pressure, heart rate, etc.), patient record information (e.g., medical history, age, weight, etc.). In addition, first monitor 120 and second monitor 122 may be configured to display procedure specific information (e.g., duration of procedure, catheter or guide wire position, volume of medicine or contrast agent delivered, etc.). Monitor 120 and monitor 122 may be configured to display information regarding the position the guide catheter. Further, monitor 120 and monitor 122 may be configured to display information to provide the functionalities associated with controller 134 (shown in FIG. 4) discussed below. In another embodiment, user interface 126 includes a single screen of sufficient size to display one or more of the display components and/or touch screen components discussed herein.

Catheter procedure system 100 also includes an imaging system 104 located within lab unit 106. Imaging system 104 may be any medical imaging system that may be used in conjunction with a catheter based medical procedure (e.g., non-digital x-ray, digital x-ray, CT, MRI, ultrasound, etc.). In an exemplary embodiment, imaging system 104 is a digital x-ray imaging device that is in communication with workstation 116. In one embodiment, imaging system 104 may include a C-arm (not shown) that allows imaging system 104 to partially or completely rotate around patient 102 in order to obtain images at different angular positions relative to patient 102 (e.g., sagittal views, caudal views, anterior-posterior views, etc.).

Imaging system 104 may be configured to take x-ray images of the appropriate area of patient 102 during a particular procedure. For example, imaging system 104 may be configured to take one or more x-ray images of the heart to diagnose a heart condition. Imaging system 104 may also be configured to take one or more x-ray images during a catheter based medical procedure (e.g., real time images) to assist the user of workstation 116 to properly position a guide wire, guide catheter, stent, etc. during the procedure. The image or images may be displayed on first monitor 120 and/or second monitor 122. In particular, images may be displayed on first monitor 120 and/or second monitor 122 to allow the user to, for example, accurately move a guide catheter into the proper position.

Figure 2:
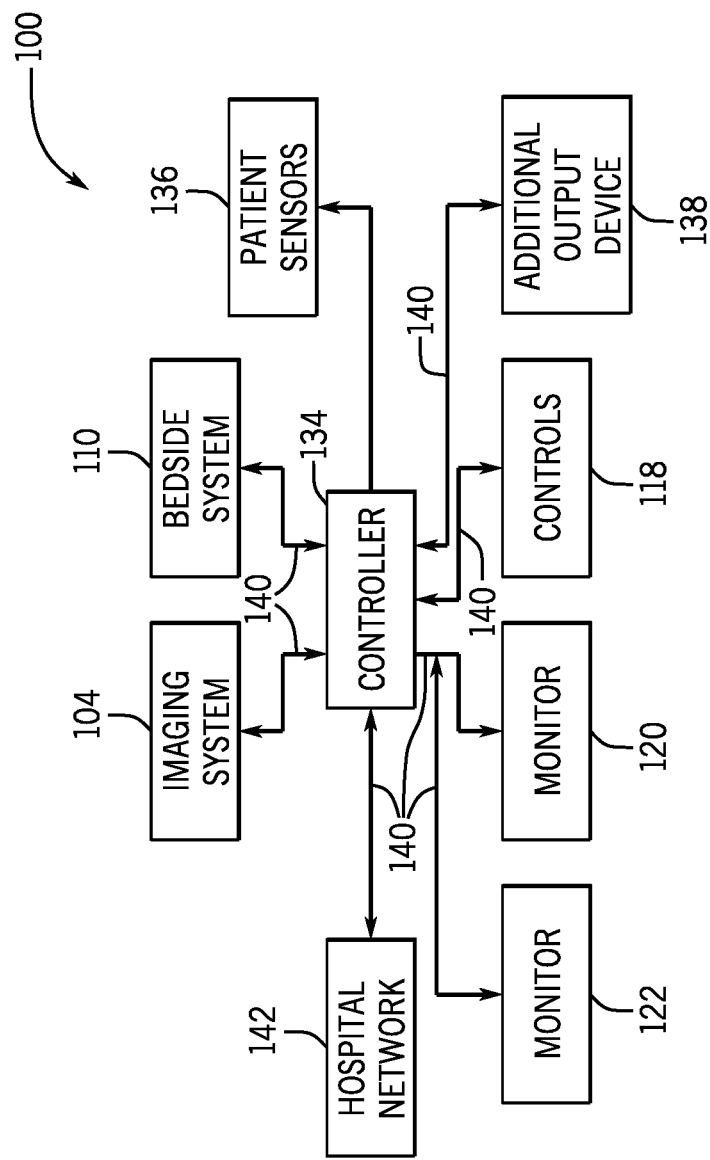
FIG. 2 a schematic block diagram of a catheter procedure system in accordance with an embodiment.

Referring to FIG. 2, a block diagram of catheter procedure system 100 is shown according to an exemplary embodiment. Catheter procedure system 100 may include a control system, shown as controller 134. Controller 134 may be part of workstation 116. Controller 134 may generally be an electronic control unit suitable to provide catheter procedure system 100 with the various functionalities described herein. For example, controller 134 may be an embedded system, a dedicated circuit, a general purpose system programed with the functionality described herein, etc. Controller 134 is in communication with one or more bedside systems 110, controls 118, monitors 120 and 122, imaging system 104 and patient sensors 136 (e.g., electrocardiogram ("ECG") devices, electroencephalogram ("EEG") devices, blood pressure monitors, temperature monitors, heart rate monitors, respiratory monitors, etc.). In various embodiments, controller 134 is configured to generate control signals based on the user's interaction with controls 118 and/or based upon information accessible to controller 134 such that a medical procedure may be performed using catheter procedure system 100. In addition, controller 134 may be in communication with a hospital data management system or hospital network 142 and one or more additional output devices 138 (e.g., printer, disk drive, cd/dvd writer, etc.).

Communication between the various components of catheter procedure system 100 may be accomplished via communication links 140. Communication links 140 may be dedicated wires or wireless connections. Communication links 140 may also represent communication over a network. Catheter procedure system 100 may be connected or configured to include any other systems and/or devices not explicitly shown. For example, catheter procedure system 100 may include IVUS systems, image processing engines, data storage and archive systems, automatic balloon and/or stent inflation systems, medicine injection systems, medicine tracking and/or logging systems, user logs, encryption systems, systems to restrict access or use of catheter procedure system 100, etc.

As mentioned, controller 134 is in communication with bedside system 110 and may provide control signals to the bedside system 110 to control the operation of the motors and drive mechanisms used to drive the percutaneous intervention devices (e.g., guide wire, catheter, etc.). The bedside system 110 may include, for example, a guide wire axial drive mechanism that provides for advancement and/or retraction of a guide wire, a working catheter axial drive mechanism that provides for advancement and/or retraction of a working catheter and a guide wire rotational drive mechanism that is configured to cause a guide wire to rotate about its longitudinal axis. In one embodiment, the various drive mechanism are housed in a cassette 114 (shown in FIG. 1).

Figure 3:
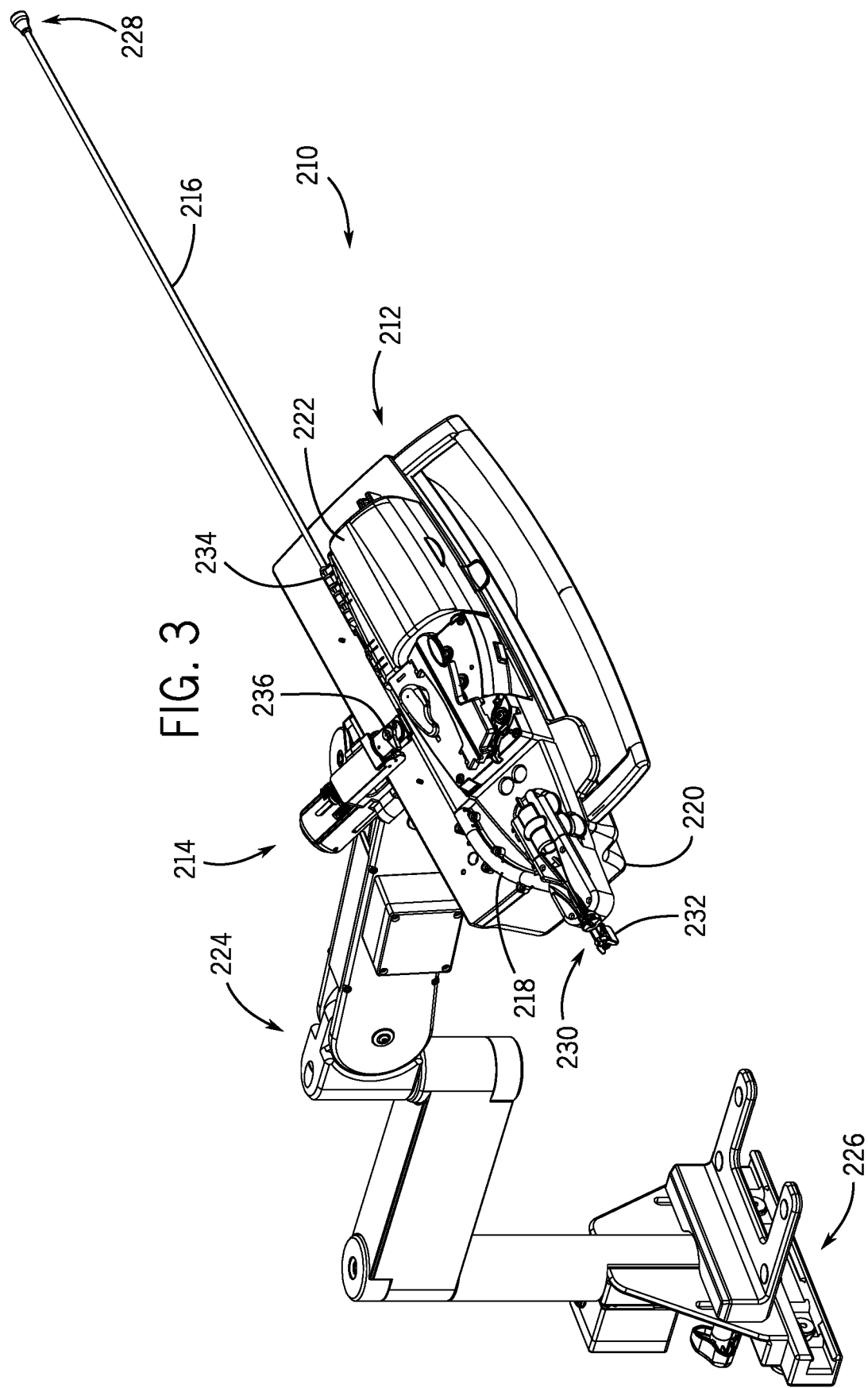
FIG. 3 is an isometric view of a bedside system of a catheter procedure system in accordance with an embodiment.

FIG. 3 is an isometric view of a bedside system of a catheter procedure system in accordance with an embodiment. In FIG. 3, a bedside system 210 includes a robotic mechanism 212 that may be used to robotically move an elongated medical device. The robotic mechanism 212 is movable relative to a base 214. The robotic mechanism 212 includes a robotic drive base 220 movable relative to base 214 and a cassette 222 that is operatively secured to robotic drive base 220. In one embodiment, base 214 is secured to an articulating arm 224 that allows a user to position robotic mechanism 212 proximate a patient. In an embodiment, base 214 is the distal portion of the articulating arm 224. Articulating arm 224 is secured to a patient bed by a rail clamp or a bed clamp 226. In this manner, base 214 is secured to a patient bed. By manipulation of articulated arm 224, the base 214 is placed in a fixed location relative to a patient that lies upon the patient bed. The arms of articulated arm can be fixed once the desired location of robotic mechanism 212 is set relative to the patient.

As used herein, the direction distal is the direction toward the patient and the direction proximal is the direction away from the patient. The term up and upper refers to the general direction away from the direction of gravity and the term bottom, lower and down refers to the general direction of gravity. The term front refers to the side of the robotic mechanism that faces a user and away from the articulating arm. The term rear refers to the side of the robotic mechanism that is closest to the articulating arm. The term inwardly refers to the inner portion of a feature. The term outwardly refers to the outward portion of a feature.

Bedside system 210 also includes a flexible track 216 that is movable along a rigid guide track 218 having a non-linear portion. The flexible track 216 includes a proximal end 228 and a distal end 230. The flexible track 216 supports an elongated medical device such as a guide catheter so that the guide catheter can be advanced into the patient without buckling. In one embodiment, cassette 222 includes structure that defines rigid guide 218. In another embodiment, base 214 alone or in combination with cassette 222 includes structure that defines rigid guide 218.

Figure 4:
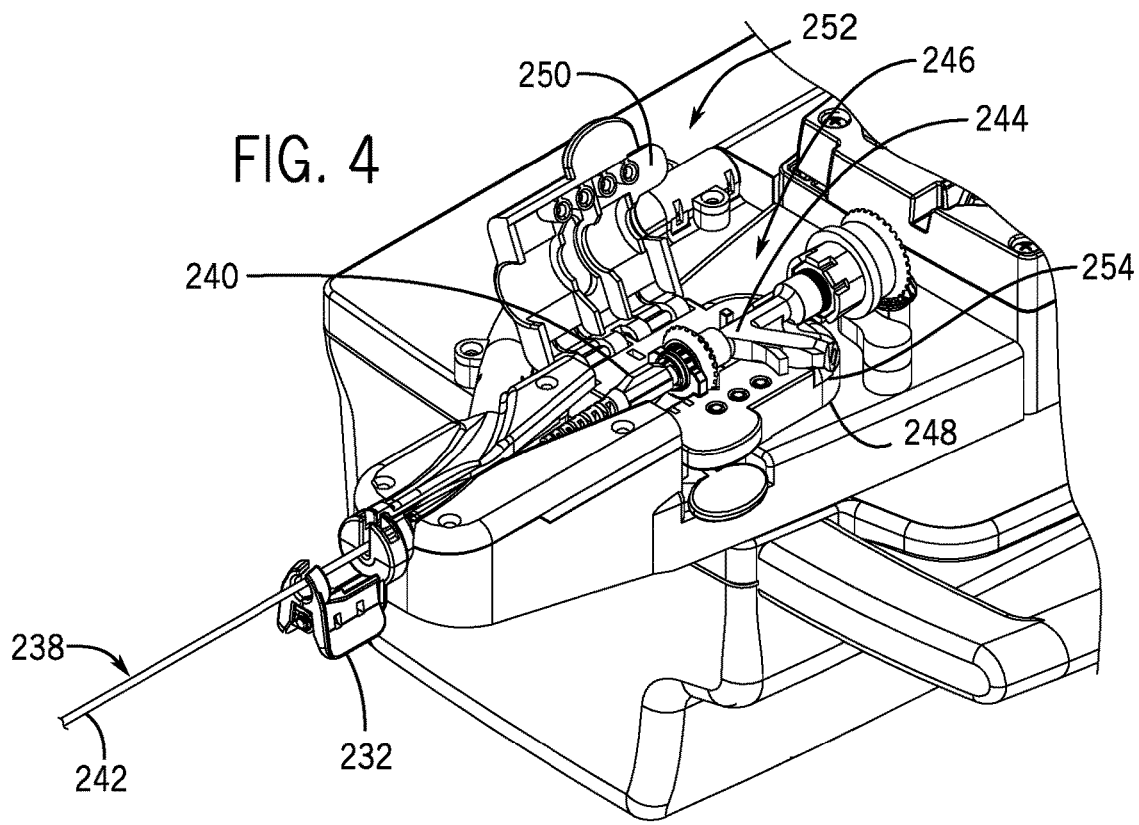
FIG. 4 is an isometric view of the front portion of the catheter procedure system of FIG. 3 with Y-connector support cover in a raised position in accordance with an embodiment.
Figure 5:
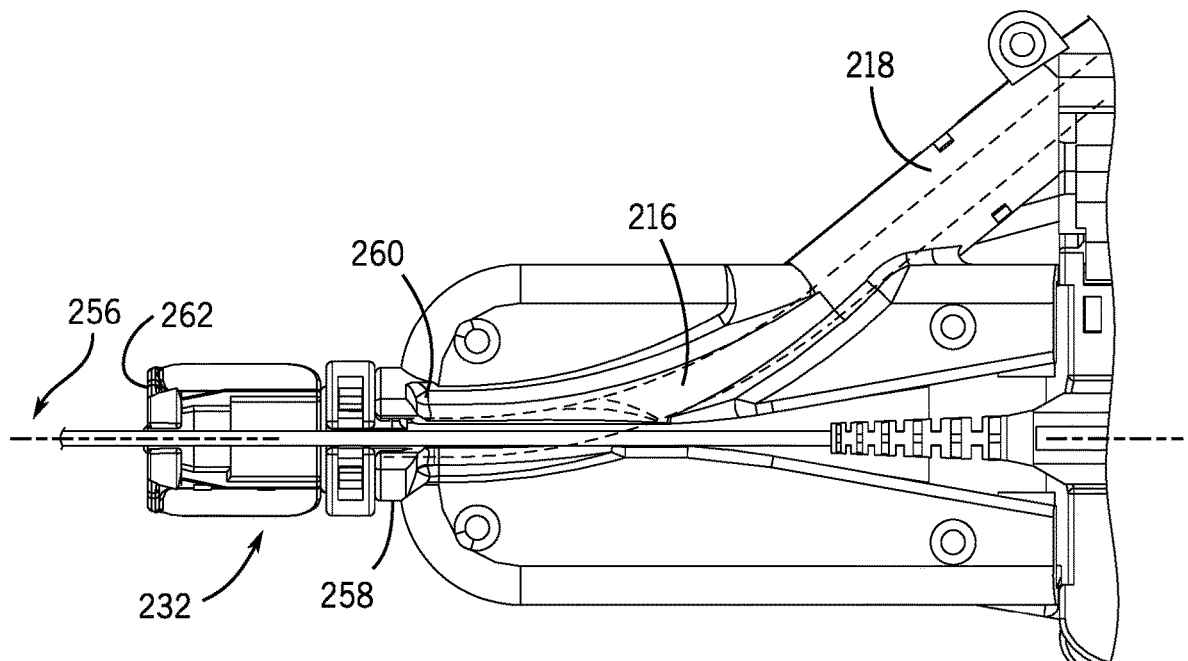
FIG. 5 is a top plan view of the front portion of the catheter procedure system of FIG. 3 with the guide catheter in an engaged position in accordance with an embodiment.

Referring to FIGS. 4 and 5, an elongated medical device such as a guide catheter 238 is operatively secured to the robotic mechanism 212 through the cassette 222. Guide catheter 238 includes a proximal end 240 and an opposing distal end 242. In one embodiment, the proximal end 240 of guide catheter 238 may be operatively secured to a Y-connector 244 and a Y-connector engagement mechanism 246. The Y-connector 244 may be, for example, a hemostasis valve that is secured to cassette 222 by the Y-connector engagement mechanism 246. The y-connector engagement mechanism 246 includes a Y-connector base 248 that is part of cassette 222 and an enclosure member 252 that includes a lid 250 and a support member 254. The y-connector base 248 includes a guide catheter drive mechanism (not shown) located in the cassette 222 which in turn is operatively connected to robotic base 220. The guide catheter drive mechanism includes a drive mechanism that operatively engages and rotates guide catheter 238 along its longitudinal axis based on commands provided by a controller (such as controller 134 shown in FIG. 2).

Referring to FIG. 5, the guide catheter 238 maintains a linear position along its longitudinal axis 256 within cassette 222 and for at least a certain distance distal cassette 222. In one embodiment, longitudinal axis 256 corresponds to the longitudinal axis of cassette 222. During a medical procedure such as a percutaneous coronary intervention (PCI), guide catheter 238 is used to guide other elongated medical devices such as a guide wire and balloon stent catheter into a patient to conduct, for example, an exploratory diagnosis or to treat a stenosis within a patient's vascular system. In one such procedure, the distal end 242 of the guide catheter 238 is seated within the ostium of a patient's heart. Robotic mechanism 212 drives a guide wire and/or a working catheter such as a balloon stent catheter in an out of a patient. The guide wire and working catheter are driven within the guide catheter 238 between the distal end of the robotic mechanism 212 and the patient. In one embodiment, longitudinal axis 256 is the axis 3 about which cassette 222 causes rotation of a guide wire and the axis along which cassette 222 drives the guide wire along its longitudinal axis and drives a working catheter such as a balloon stent catheter along its longitudinal axis.

Figure 6:
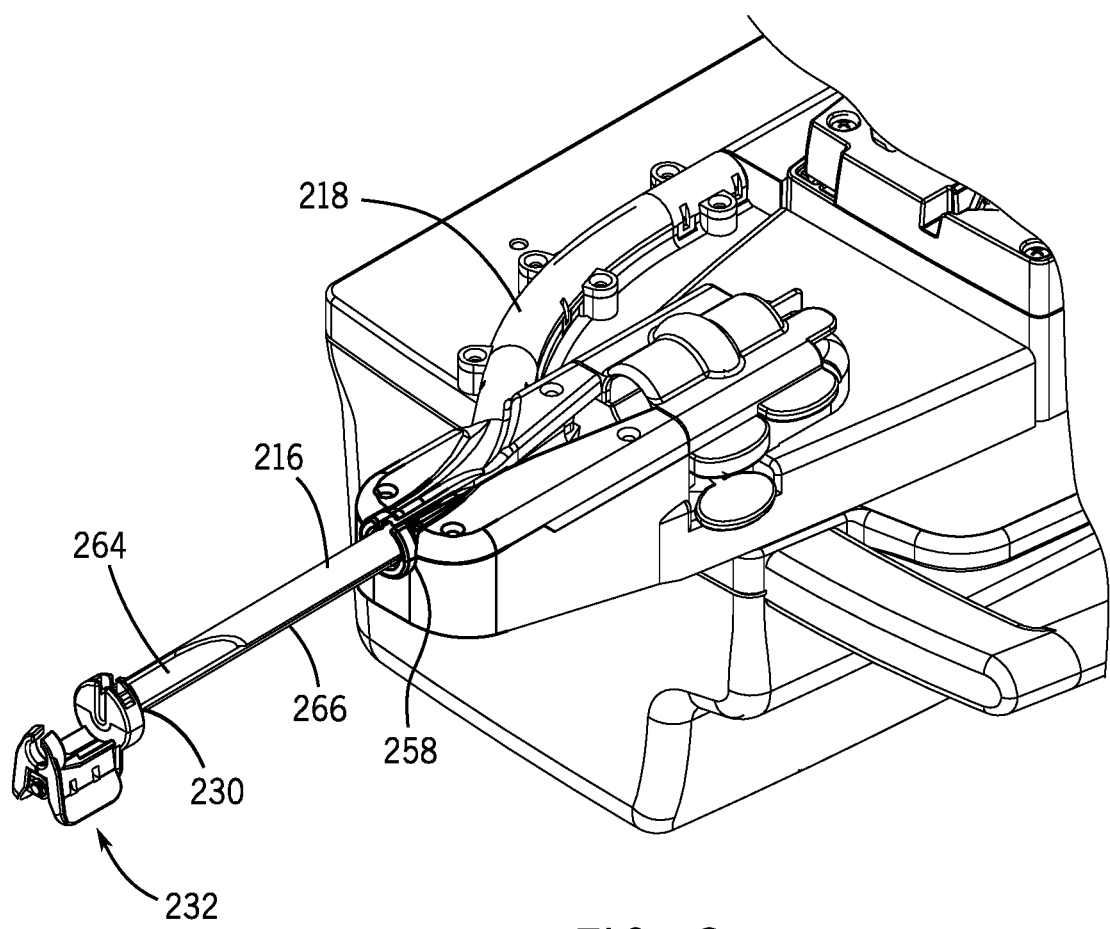
FIG. 6 is an isometric view of the front portion of the catheter procedure system of FIG. 3 with the flexible track in an extended position in accordance with an embodiment.

Referring to FIGS. 5 and 6, a collar 258 is formed at the distal end 260 of rigid guide 218. The terminal end 230 of flexible track 216 is secured to a sheath clip 232 which is releasably connected to cassette 222. The rigid guide 218 includes an inner channel through which the flexible track 216 moves relative to rigid guide 218. The flexible track 216 includes an opening 264 located adjacent the terminal distal end 230 of flexible track 216. When distal end 230 of flexible track 216 is positioned adjacent collar 258, the opening 264 extends from collar 258 toward the area in which rigid guide 218 begins an arcuate path away from longitudinal axis 248. In one embodiment, the arcuate path forms an s-curve having at least one point of inflection along the arcuate path. The opening 264 provides a path for guide catheter 238 to be placed into the hollow cavity of flexible track 216. Opening 264 tapers to a slit 266 that extends substantially the entire length of flexible track 216. In one embodiment, slit 266 extends from opening 264 a distance sufficient to allow guide catheter 238 to enter and exit an interior portion of flexible track 216 throughout the entire intended operation of the robotic catheter system.

Referring to FIG. 3, the flexible tack 216 is initially positioned within the rigid guide 218 by feeding distal end 230 of flexible track 216 into proximal opening 234 of rigid guide 218 until the distal end 230 of flexible track 216 extends beyond collar 258 of rigid guide 218. The distal end 230 of flexible track 216 is operatively connected to the sheath clip 232. The rigid guide includes a linear portion beginning at proximal opening 234 and a non-linear portion. In one embodiment, the non-linear portion is an arcuate portion having at least one point of inflection. FIG. 6 shows a portion of the flexible track 216 extending beyond collar 258. Since flexible track 216 is formed of a flexible material having a modulus of elasticity that is less than the modulus of elasticity of the rigid guide material, flexible track 216 moves along the curved non-linear portion of the channel defined by rigid guide 218.

Referring to FIGS. 7 and 8, to perform a procedure the sheath clip 232 is pulled by a user away from cassette 222 in a direction along longitudinal axis 256 until the distal end 262 of sheath clip 232 is proximate the patient. In one embodiment, an introducer (not shown) is secured to the distal end 262 of sheath clip 232. The introducer is a device that is secured to a patient to positively position the introducer to the patient to allow insertion and removal of elongated medical devices such as a guide catheter, guide wire and/or working catheter into the patient with minimal tissue damage to the patient. Once the operator has pulled the sheath clip 232 and accompanying flexible track 216 toward the patient such that the introducer is proximate the patient, the flexible track 216 is locked in position by a locking clamp 236. The locking clamp 236 secures the flexible track 216 to base 214 such that a portion of flexible track 216 is in a fixed position relative to the patient bed and the patient to the extent the patient lies still on the patient bed.

Figure 11:
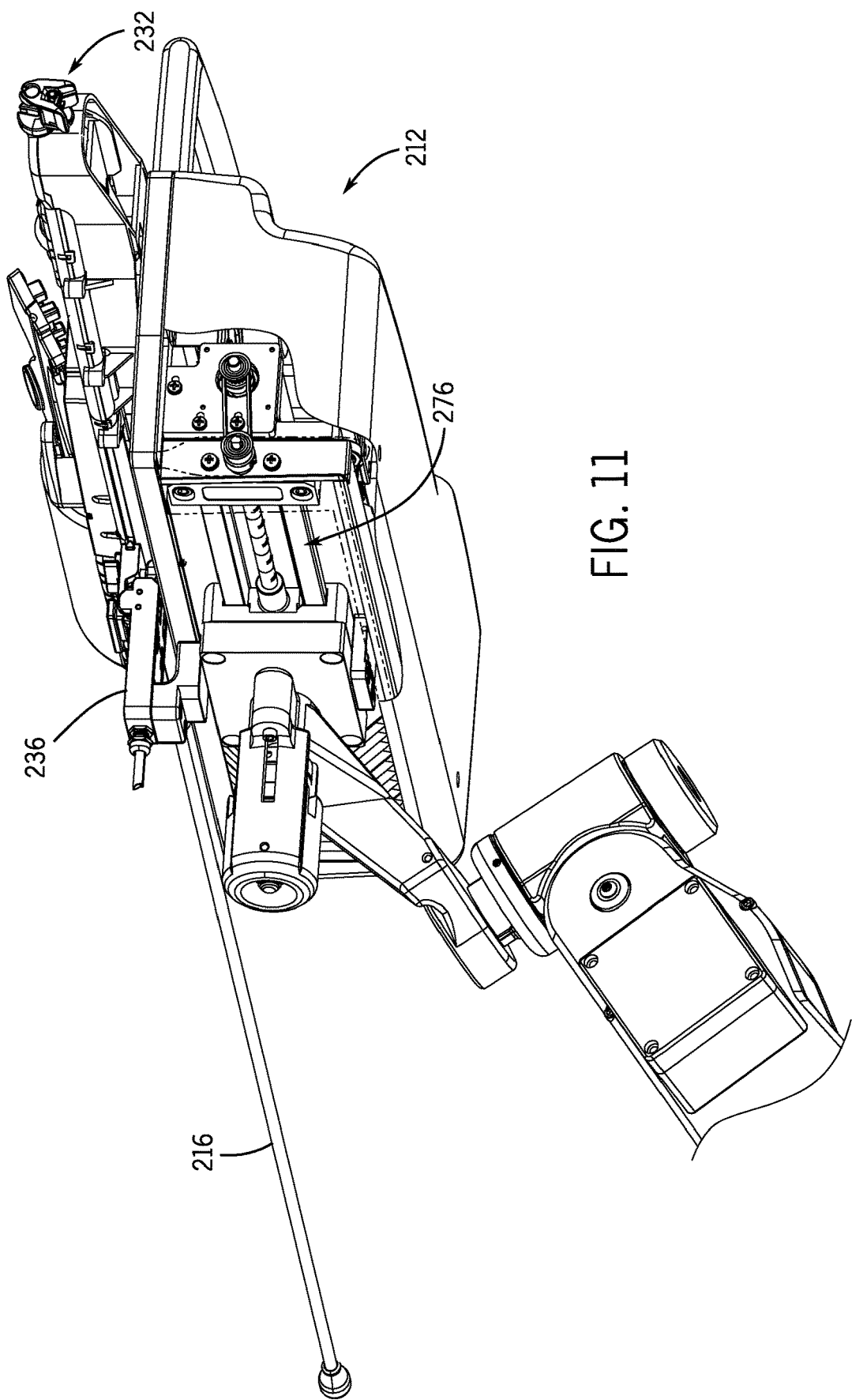
FIG. 11 is a rear isometric view of the catheter procedure system with a linear drive in accordance with an embodiment.

Referring to FIG. 11, robotic mechanism 212 includes a linear drive mechanism 276. The linear drive mechanism 276 shown in FIG. 11 includes a linear slide that is robotically controlled by a user through a remote workstation (for example, workstation 116 shown in FIG. 1). The linear drive mechanism 276 drives robotic mechanism 212 along longitudinal axis 256. Since rigid guide 218 is fixed relative to robotic mechanism 212, the rigid guide 218 and robotic mechanism 212 move relative to the flexible track 216 as the robotic mechanism 212 moves along the longitudinal axis 256.

Referring to FIG. 7 and FIG. 8, the operation and movement of flexible track 215 relative to rigid guide 218 will be described. Referring to FIG. 7, flexible track 216 is shown in the installation first position in which guide catheter 238 is positioned within sheath clip 232 and flexible track opening 264 as described above. Referring to FIG. 8, once sheath clip 232 has been released from the cassette 222, the sheath clip 232 and distal end 230 of the flexible track 216 are pulled by a user away from cassette 222 such that the distal end 262 of the sheath clip 232 is proximate the entry point of the patient in which a percutaneous intervention will occur. The locking clamp 236 operatively clamps a portion of flexible track 216 so that flexible track 216 is fixed relative to base 214.

Referring to FIGS. 7 and 8, the portion of flexible track 216 that is positioned within the arcuate portion of rigid guide 218 is pulled out of the distal end 262 of rigid guide 218 in a direction generally along longitudinal axis 256. Similarly, a portion 268 of flexible track 216 that was external to and not located within the arcuate portion of rigid guide 218 is pulled into the arcuate portion of rigid guide 218 and depending on how far the terminal distal end 230 of the flexible track 216 is pulled toward the patient, portion 268 of flexible track 216 will enter the arcuate portion of rigid guide and may extend therefrom. Stated another way, flexible track 216 includes three general regions that change with the operation of the guide catheter system. First, a proximal region that includes the flexible track portion from the proximal end 228 of flexible track 216 to the proximal end 270 of the arcuate portion of rigid guide 218. Flexible track 216 includes a second portion located between the proximal end 270 of the arcuate portion of rigid guide 218 and the distal end 272 of the arcuate portion of rigid guide 218 proximate collar 258. Flexible track 216 includes a third region that extends from collar 258 of rigid guide 218 in a direction defined by a vector generally along longitudinal axis 256, where the vector has a beginning at the Y-connector and extends in a direction toward collar 258. The first region and second region of flexible track 216 as described above is offset from and not in line with longitudinal axis 256. The third portion of flexible track 216 is generally coaxial with longitudinal axis 256 as flexible track 216 exits collar 258 of rigid guide 218.

During one type of intervention procedure, guide catheter 238 is inserted into a patient's femoral artery through an introducer and positioned proximate the coronary ostium of a patient's heart. An operator may wish to relocate the distal end of the guide catheter robotically. Referring to FIGS. 9 and 10, the control of the distal end of guide catheter 238 and the movement of the robotic mechanism 212 and rigid guides 218 relative to the flexible track 216 will be described. Referring to FIG. 9, guide catheter 238 has a distal portion which extends beyond the distal end 262 of sheath clip 232 in order to extend the terminal end of guide catheter 238 in a direction away from the terminal distal end 262 of the sheath clip 232. As noted above, the distal end of guide catheter 238 may be placed proximate the ostium of a patient. The robotic control of the distal end of the guide catheter 238 is accomplished by movement of robotic drive mechanism 212 relative to base 214 and flexible track 216 by linear drive 276. The guide catheter 238 is located within the channel of the flexible track 216 from cassette 222 until the sheath clip 232.

If during a PCI procedure the guide catheter begins to slip out of the ostium, it is possible to extend the distal end of guide catheter 238 back into the patient ostium by robotically moving the robotic mechanism 212 towards the patient. In doing so, the distal end of guide catheter 238 is moved toward the patient reinserting or seating the distal end of the guide catheter into the patient's ostium as one example. As the robotic drive mechanism 212 is moved along longitudinal axis 256, the rigid guide 218 is moved relative to the flexible track 216. The portion of flexible track 216 that is located within the arcuate section of rigid guide 216 changes as the robotic mechanism 212 and rigid guide 218 are moved. The portion of the flexible track 218 that is located in the rigid guide is moved toward and away from longitudinal axis 256 depending on the direction that the robotic drive mechanism 212 is moving. Guide catheter 238 moves into or out of the section of flexible track 216 that is moving in and out of the arcuate portion of rigid guide 218. In this manner, the portion of guide catheter 238 between cassette 222 and the sheath clip 232 is always located within the channel of flexible track 216. In this manner, guide catheter 238 may be manipulated within flexible track 216 without buckling or causing other non-desirable movement during a percutaneous intervention procedure.

Referring to FIGS. 9 and 10, the position of the flexible track 216 with respect to rigid guide 218 will be described as it related to a single section A on flexible track 216. In one example, section A on flexible track 216 is located distal collar 258 of rigid guide 218. When an operator determines to insert guide catheter 238 further into or toward a patient in a direction away from collar 258, an input device is manipulated by the user at a remote workstation that drives robotic drive 212 distally along longitudinal axis 256 by activating linear drive 276. The proximal end of guide catheter 238 is longitudinally fixed in cassette 222 so that as the robotic drive 212 including cassette 222 is moved relative to base 214 and flexible track 216 by linear drive 276 in a direction toward the patient, the guide catheter 238 moves distally along longitudinal axis 256. As a result, the distal end of guide catheter 238 moves toward and/or into the patient.

As the robotic mechanism 212 is moved along longitudinal axis 256, section A of flexible track 216 moves into the arcuate portion of rigid guide 218 through collar 258 and along the arcuate portion of rigid guide until section A of the flexible track 216 is adjacent the proximal end of rigid guide 218. In this manner, distal end 230 of flexible track 216 remains in a constant position but section A of flexible track 216 is moved out of or offset to the longitudinal axis 256. As section A moves into the arcuate channel defined by the rigid guide 218, the guide catheter 238 enters the channel or hollow lumen of the flexible track 216 through the slit adjacent in the engagement zone proximal to collar 258. In this manner, flexible track 216 provides continual support and guidance for the guide catheter 238 between the collar 258 and the patient as the distal end of guide catheter 238 is moved toward and away from the patient.

Similarly, if the operator desires to retract the distal end of the guide catheter 238 from within the patient, the user provides a command to the linear drive 276 through the remote workstation to move robotic drive mechanism 212 in a direction away from the patient. In this way, section A of the flexible track 216 would enter the proximal end of the arcuate portion of the rigid guide and be guided within the channel of the rigid guide 218 until section A exits the distal end of the rigid guide 218. The guide catheter 238 would enter the slit at section A or stated another way, a portion of the guide catheter 238 would enter the flexible track 216 via the portion of the slit that is located within the concentric circle taken at section A of the flexible track 216. Note that although sections of the flexible track are positioned in different regions of the rigid guide as the robotic mechanism is moved toward and away from the patient the proximal end and the distal end of the flexible track remain in a fixed location as the robotic mechanism is moved along the longitudinal axis.

Figure 12:
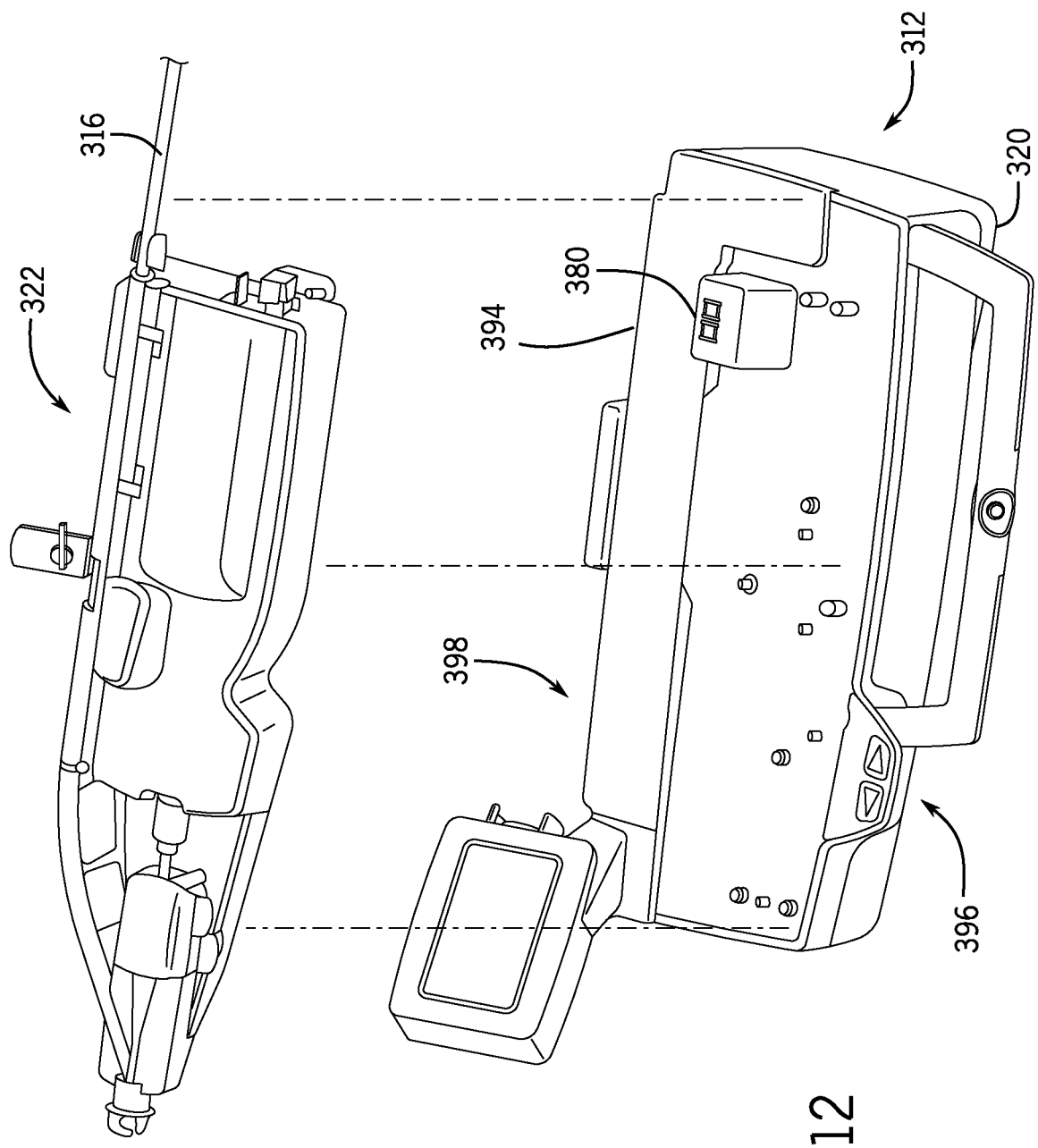
FIG. 12 is a perspective view of the catheter procedure system with the cassette in a pre-assembly position relative to the robotic drive base in accordance with an embodiment.
Figure 13:
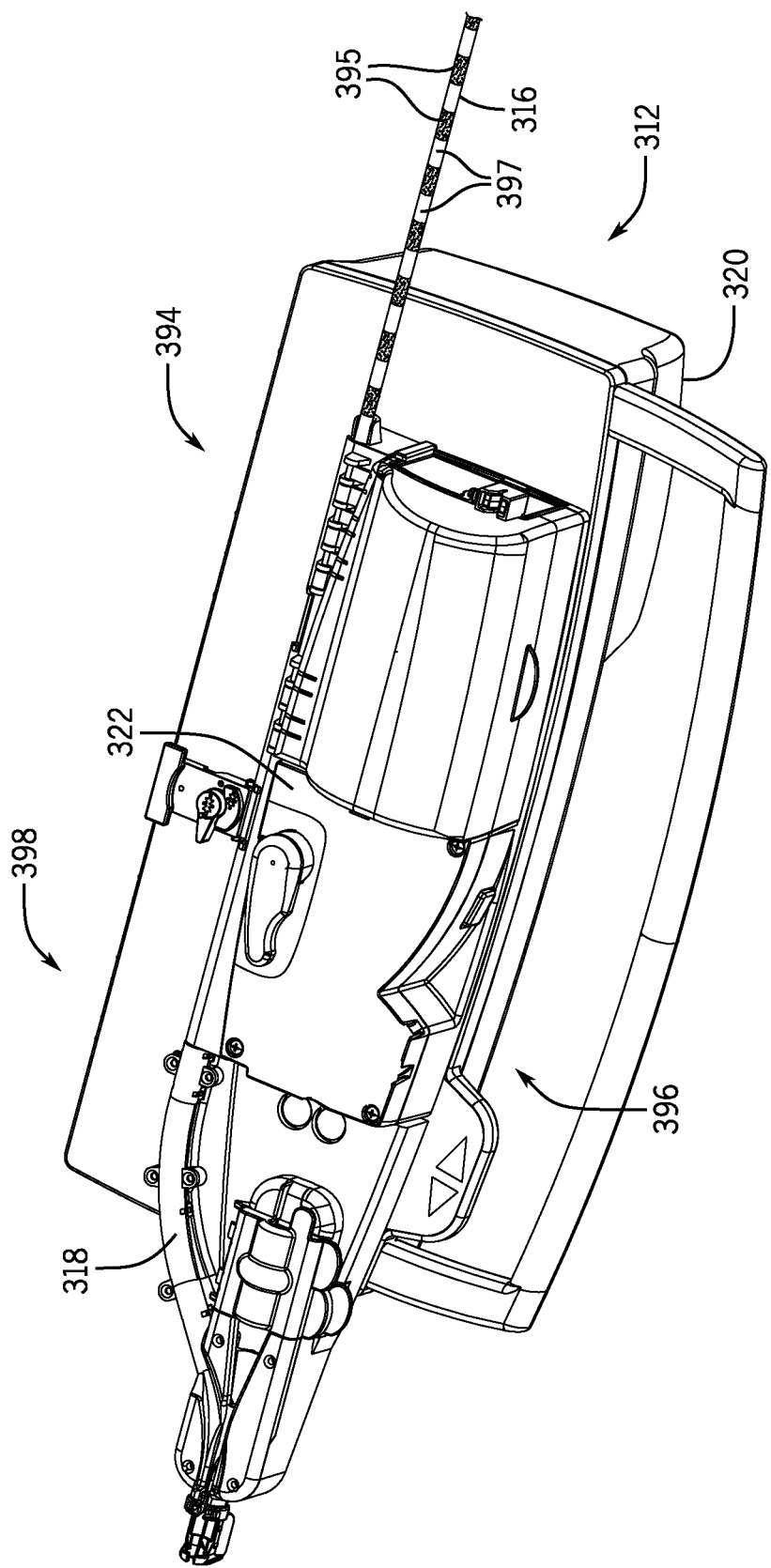
FIG. 13 is a perspective view of the cassette mounted to the robotic drive base in accordance with an embodiment.
Figure 14:
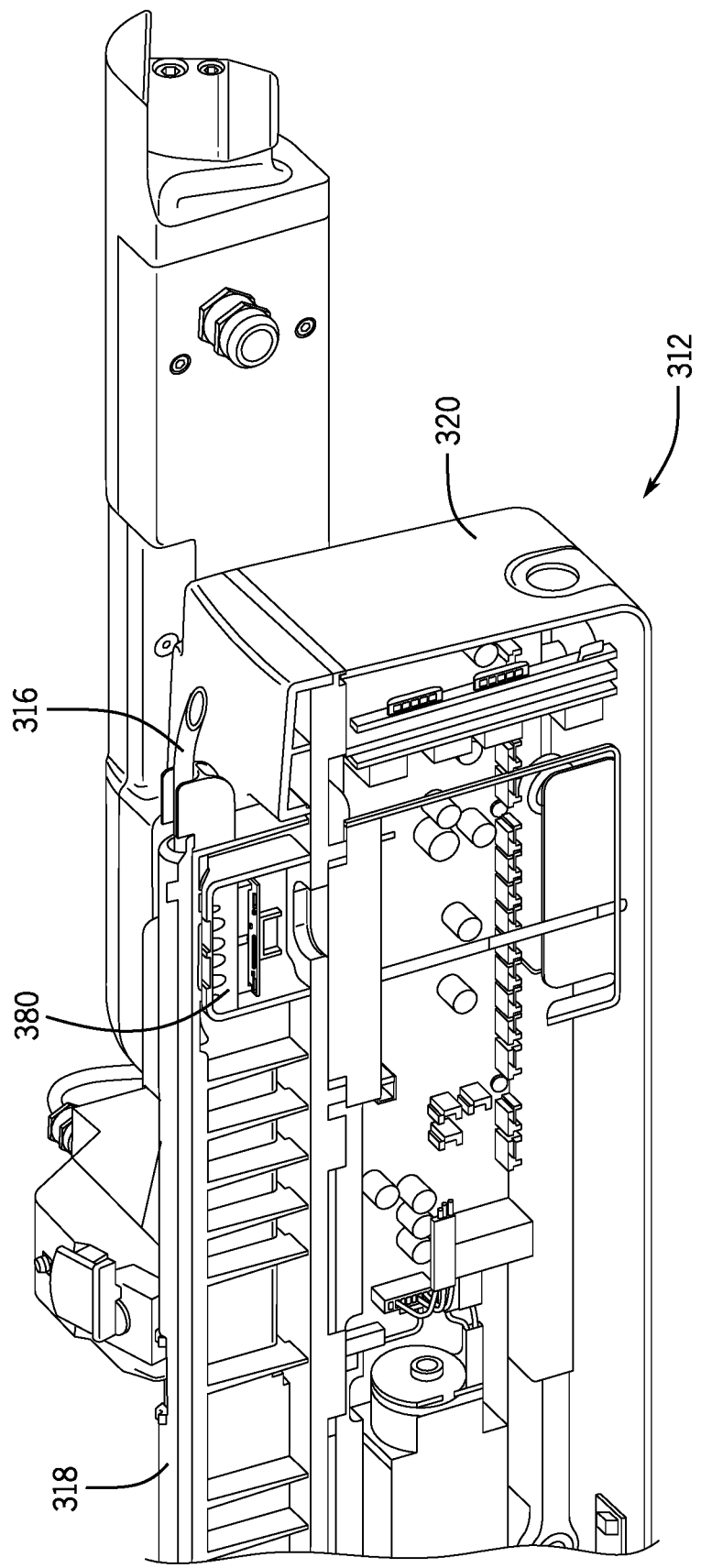
FIG. 14 is a front side cross sectional view of the robotic drive base and cassette showing the position detector in accordance with an embodiment

Robotic mechanism 212 may also include a position sensor to determine the distance the distal end 230 of the flexible track 216 has been pulled away from the cassette 222 (e.g., the distance from collar 258) along the longitudinal axis 256. The position information regarding the distal end 230 of the flexible track 216 may be used to control or limit the distance the robotic mechanism 212 moves along the longitudinal axis 256 toward the patient. FIG. 12 is an exploded view of a bedside system with a cassette in a pre-assembly position relative to the robotic drive base in accordance with an embodiment. A front side of the robotic mechanism 312 is generally designated by 396 and a rear side of the robotic mechanism 312 is generally designated by 398. A position detector 380 is coupled to the robotic drive base 320 of the robotic mechanism 312. Position detector 380 is located at a proximal end 394 of the robotic drive base 320. The position detector 380 is positioned on the robotic drive base 320 so that it sits beneath a proximal portion of flexible track 316 when the cassette 322 is mounted on the robotic drive base 320. FIG. 13 shows the cassette 322 mounted on the robotic drive base 320 and disposed over the position detector 380. FIG. 14 is a front side cross sectional view of the robotic drive base and cassette showing the position detector in accordance with an embodiment. In FIG. 14, a front cross-sectional view of the position detector 380 is shown. Position detector 380 is mounted on the robotic drive base 320 and located beneath the flexible track 316. As discussed above, flexible track 316 passes through the rigid guide 318. As the flexible track is moved towards or away from the patient, the position detector 380 is configured to determine the amount of displacement of the distal end 230 (shown in FIG. 8) of the flexible track 316 from the cassette 322.

Figure 19:
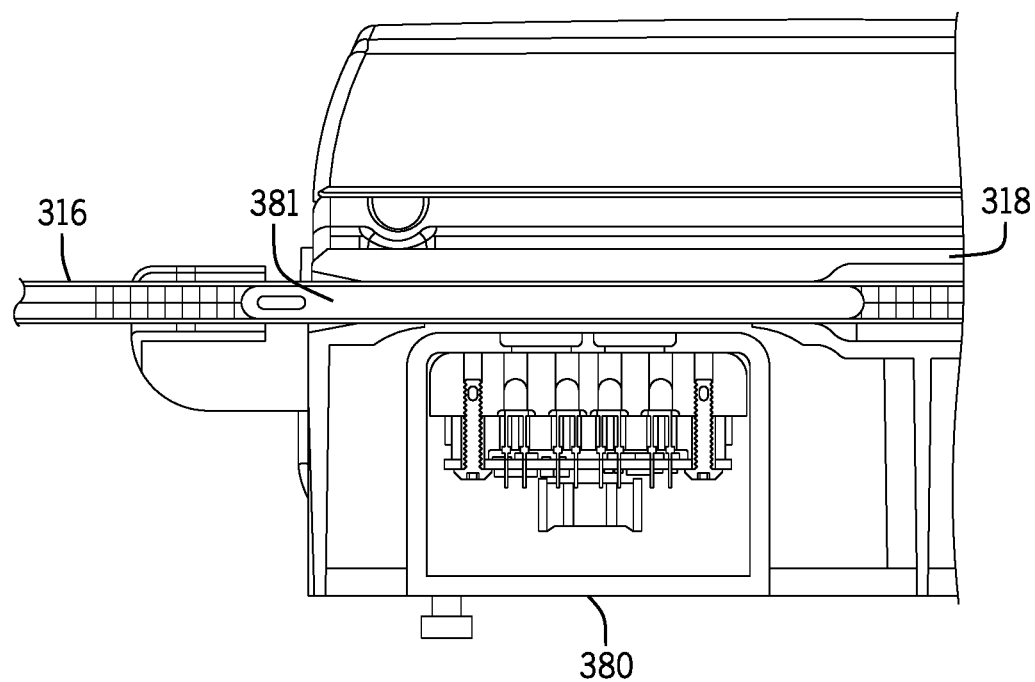
FIG. 19 is a cross-sectional view of a proximal end of the flexible track and rigid guide in accordance with an embodiment.
Figure 20:
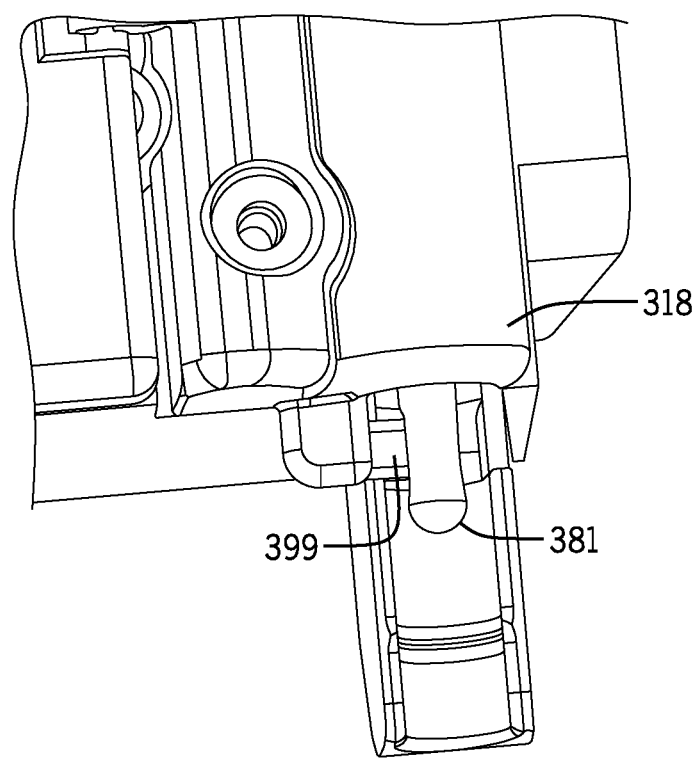
FIG. 20 is a close up top view of a proximal end of the rigid guide in accordance with an embodiment.

Position detector 380 may be, for example, an optical detector. Accordingly, the flexible track may include a pattern of reflective and non-reflective sections. Referring to FIG. 13, the flexible track 316 includes reflective lines or stripes 395 on at least a proximal portion of the flexible track 316. The reflective lines 395 are separated by non-reflective lines or section 397. The reflective lines may be created on the flexible track by, for example, printing white lines on a track formed from translucent material. In another example, the flexible track has a highly reflective opaque surface (e.g., a surface with titanium dioxide) and the non-reflective lines are added by laser etching. In another embodiment, the flexible track 316 is formed from a reflective material that is translucent and the non-reflective lines or sections may be etched on the flexible track 316 using a laser. In another embodiment, the flexible track 316 is formed from a non-reflective material and the reflective lines may be added by, for example, a printing or etching process. In an embodiment, the reflective lines 395 are evenly spaced from one another along the proximal portion of the flexible track 316 such that the reflective line width ($t_r$) equals the non-reflective line width ($t_s$). In this embodiment, the resulting resolution of the position detector 380 is B units in which the reflective line width and the non-reflective line width are equal to 2B (i.e., $t_r=t_s=2B$). Referring to FIG. 14, the position detector 380 is configured as an optical sensor that detects light reflected off of the reflective stripes or lines 395 as the flexible track 316 passes over the position detector 380. In an embodiment, the reflected light can be enhanced by providing a reflective target within proximal end of the rigid guide. FIG. 19 is a cross-sectional view of a proximal end of the flexible track and rigid guide in accordance with an embodiment. In FIG. 19, a reflective target 381 is shown located within the rigid guide 318 and flexible track 316 and above the position detector 380. The reflective target 381 is formed from a reflective material. The flexible track 316, for example, a laser etched translucent track, passes over the reflective target as the track 316 passes over the position detector 380. FIG. 20 is a close up top view of a proximal end of the rigid guide in accordance with an embodiment. In FIG. 20, the reflective target 381 may be mounted to the rigid guide 318 using a tab 399. As discussed above, the flexible track 316 includes a lengthwise slit 266 (shown in FIG. 6). The slit slides over the tab 399 as the flexible track is moved towards and away from a patient.

Figure 15:
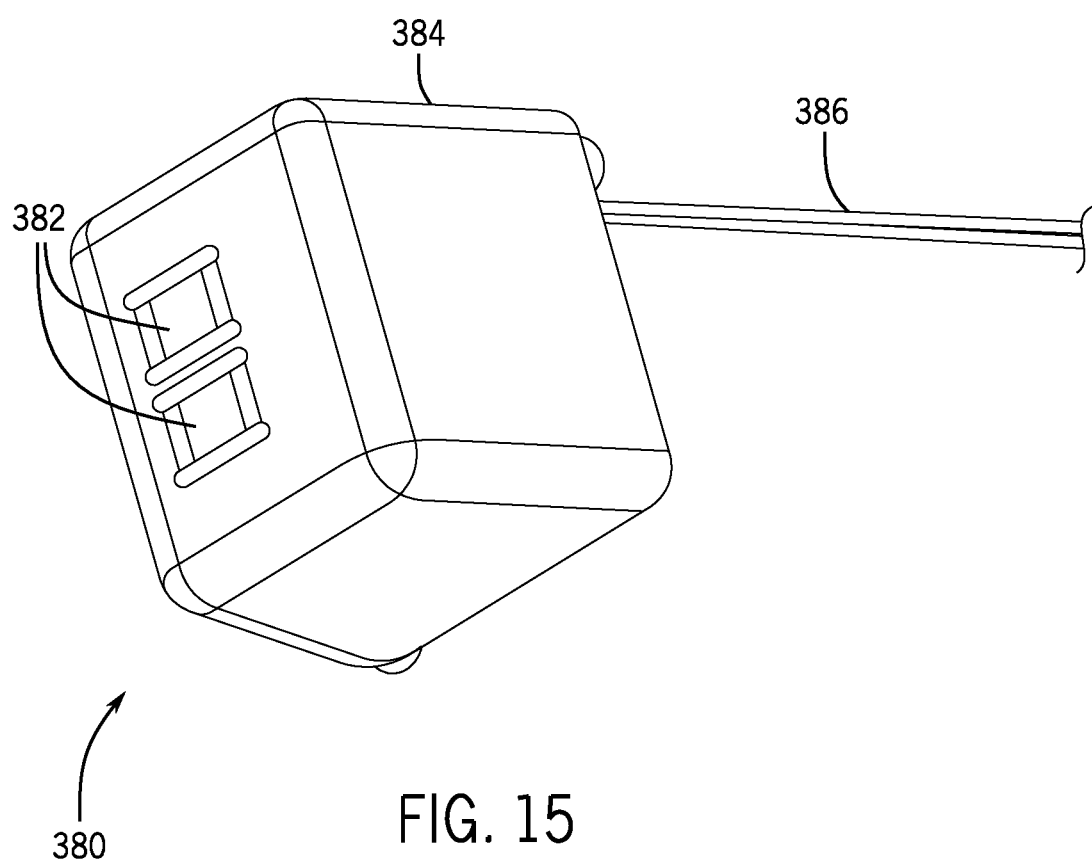
FIG. 15 is a perspective view of a position detector in accordance with an embodiment.
Figure 16:
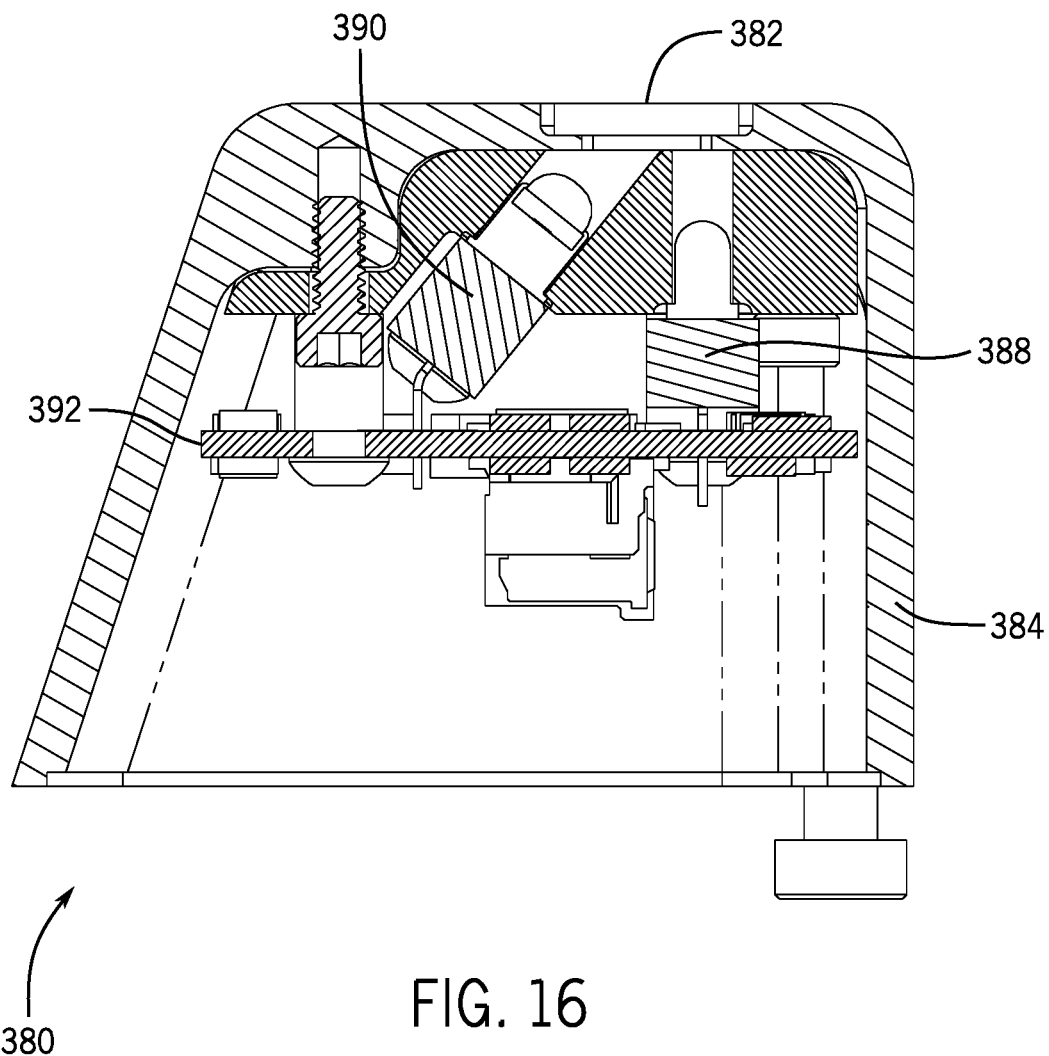
FIG. 16 is a cross-sectional view of the position detector in accordance with an embodiment.
Figure 17:
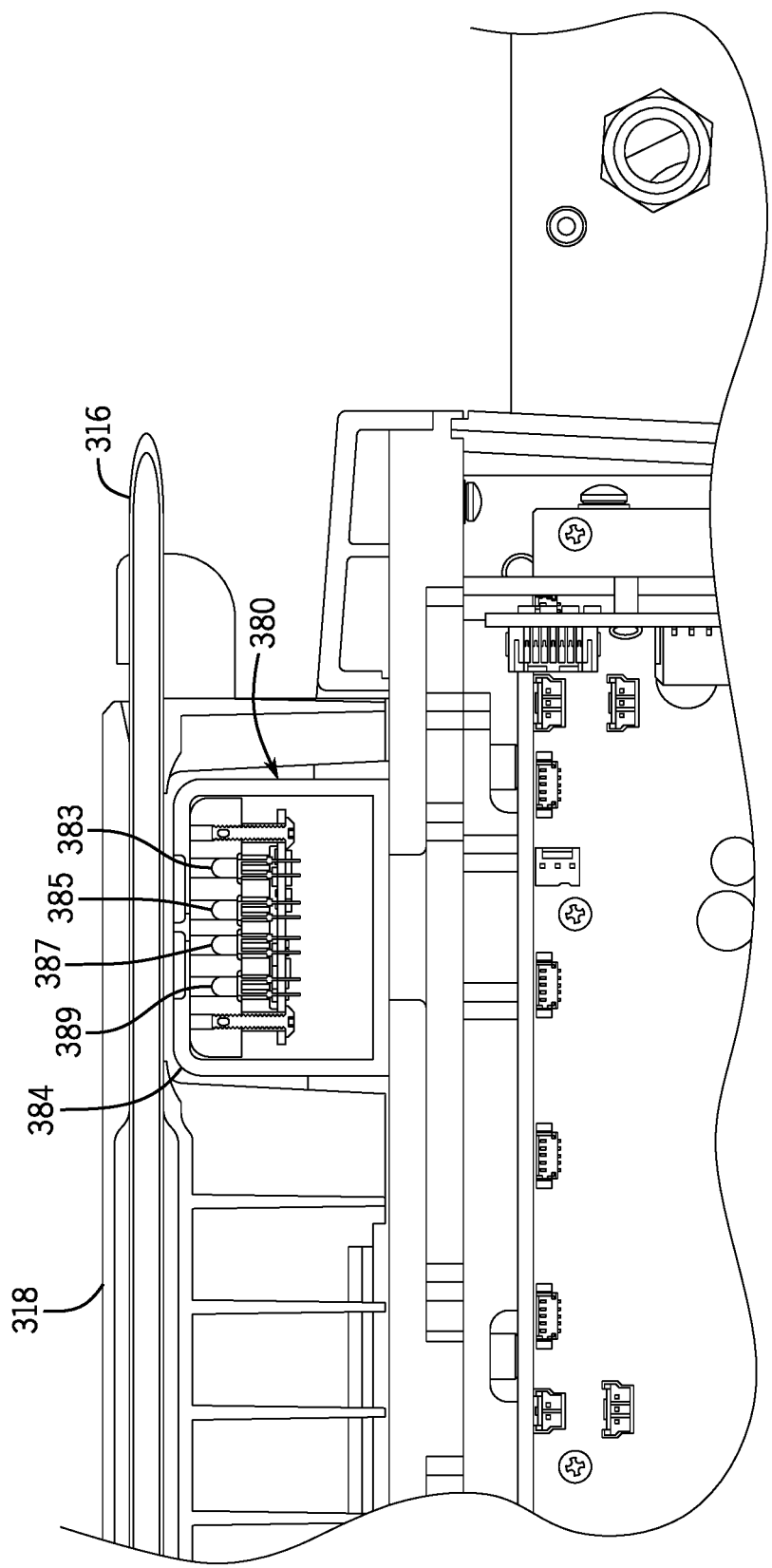
FIG. 17 is a close-up front-side cross-sectional view of the robotic drive base, cassette and position detector in accordance with an embodiment.

FIGS. 15 and 16 illustrate an exemplary position detector assembly in accordance with an embodiment. Position detector 380 includes a housing 384, windows and/or slits 382 and a reed switch 386. In one embodiment, the windows and/or slits have a width that is less than or equal to B units. The windows 382 include a transparent material such as, for example, glass with or without an anti-reflective coating. In various embodiments, the position detector may include one or more windows 382. Position detector 380 includes at least one optical detector disposed within the housing 384. FIG. 16 is a cross-sectional view of a position detector in accordance with an embodiment. The optical detector includes a light emitting diode (LED) 388 and a photo-diode 390 disposed within the housing 384 below the windows 382. The LED 388 is positioned so that light from the LED passes through the window 382 onto the flexible track 316. The photo-diode 390 is positioned so that it may detect light reflected off of the reflective lines of the flexible track 316. The LED 388 and the photo-diode 390 are coupled to a circuit board (e.g., a printed circuit board) 392. While one optical detector (i.e., the pair of LED 388 and photo diode 392) is shown in FIG. 16, in various embodiments, the position detector 380 may include more than one optical detector. FIG. 17 is a close up cross-sectional view of a robotic mechanism with a position detector in accordance with an embodiment. In FIG. 17, position detector 370 includes four optical detectors. The cross-sectional view of position detector 380 shows the LED of each of the four optical detectors, namely, a first optical detector 383, a second optical detector 385, a third optical detector 387 and a fourth optical detector 389. As discussed above, as the distal end of the flexible track 316 is moved away from or toward the cassette, the proximal end of the flexible track passes over the position sensor 380.

Figure 18:
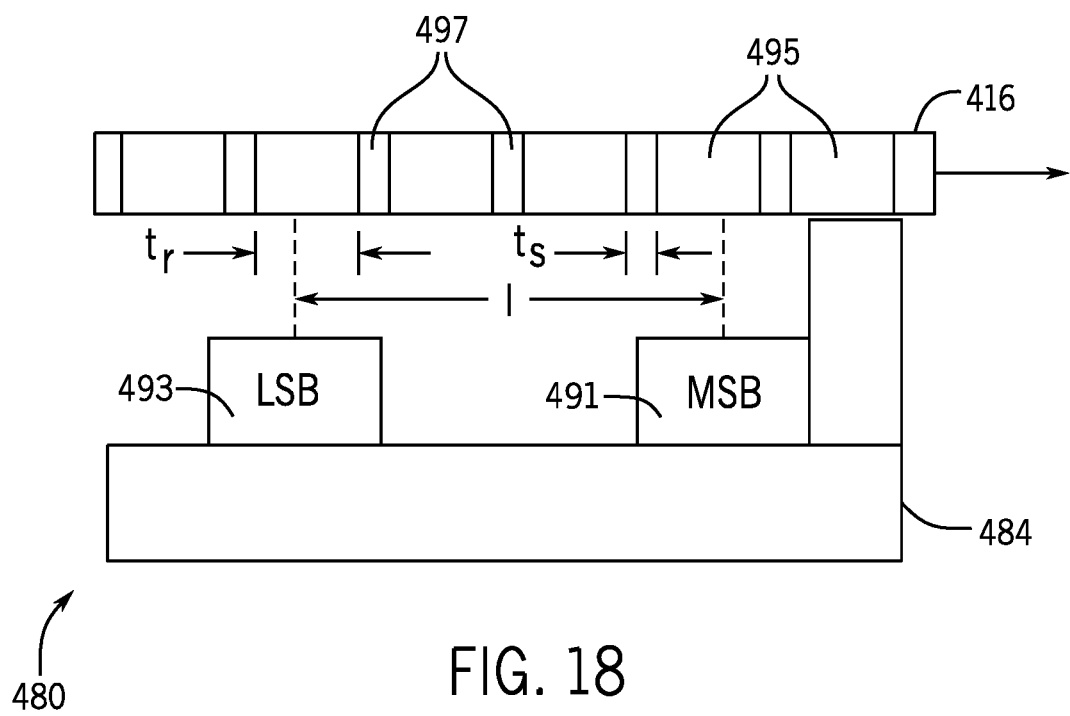
FIG. 18 is a schematic block diagram of a position detector in accordance with an embodiment.

Returning to FIG. 16, the circuit board 392 may include circuitry configured to generated signals indicating the distance the distal end of the flexible track has moved based on the reflected light detected by the photo diode 390. In one embodiment, the position detector is configured to realize a two-bit Gray Code. In one embodiment, position sensor 380 includes two optical detectors, as shown in FIG. 18 which is a block diagram of a position detector in accordance with an embodiment. In FIG. 18, a position detector 480 includes a first optical detector 491 and a second optical detector 493 disposed in a housing 484. The first optical detector 491 includes an LED and a photo diode and the second optical detector 493 includes an LED and a photo diode. To realize a two bit Gray code, the first optical detector 491 is positioned at a distal end of the housing 484 and may be designated as the most significant bit (MSB). The second optical detector 493 is positioned a distance, l (for example, l={B, 5B,9B, . . . }), from the first optical detector 487 and may be designated as the least significant bit (LSB). The flexible track 416 includes reflective lines 495 and non-reflective lines 497. Each reflective line 495 has the same width $t_r$ and are evenly spaced from one another by a distance $t_s$ (for example, $t_s$=2B units wide). In one embodiment, the reflective line width and the non-reflective line width are equal (i.e., $t_r=t_s$). The first optical detector 491 and the second optical detector 493 each generate an output voltage that increases when the photo diode detects light from the LED reflected off of the reflective lines 495 of the flexible track 416. The reflected light is used to detect the presence or absence of a reflective line 495.

When the output voltage of the first 491 or the second 493 optical detector is greater than a predetermined value (i.e., the presence of a reflective line is detected), the respective optical detector may be assigned a logic value of 1. When an output voltage of the first 491 or second 493 optical detector is less than a predetermined value (i.e., a reflective line is not detected), the optical detector may be assigned a logic value of 0. As the distal end of the flexible track 416 is moved away from or toward the cassette and the proximal portion of the flexible track 416 passes over the position detector 480, the first optical detector 491 and the second optical detector 493 will transition between logic 1 and logic 0. The distance that the distal end of the flexible track 416 is moved away from or toward the cassette may be determined based on the transitions of first 491 and second 493 optical detectors and the reflective lines 495 detected. In one embodiment, the first 491 and second 493 optical detectors will transition from (0,0)→(0,1)→(1,1)→(1,0)→(0,0) after each displacement, B units, of the distal end of the flexible track away from the cassette, The first 491 and second 493 optical detectors will transition from (1,0)→(1,1)→(0,1)→(0,0)→(1,0) after each displacement, -B units, of the distal end of the flexible track toward the cassette.

In another embodiment, four optical detectors may be used to realize a two-bit Gray Code. Referring to FIG. 17, the second optical detector 385 and the third optical detector 387 represent the LSB and MSB optical detectors, respectively. In this embodiment, the first optical detector 383 (designated as ~LSB) and the fourth optical detector 389 (designated as ~MSB) are located within the position detector 380 so that the ~LSB optical detector 383 is closest to a proximal end of the position detector 380 and the ~MSB optical detector 389 is closest to a distal end of the position detector 380. In other words, denoted from the proximal end towards the distal end of the position detector 380, the first optical detector 383 is designated as ~LSB, the second optical detector 385 is designated as LSB, the third optical detector 387 is designated as MSB and the fourth optical detector 389 is designated as ~MSB. The third optical detector 387 is positioned a distance, l (for example, l={B, 5B, 9B . . . }), from the second optical detector 385. The ~LSB optical detector 383 may be located a distance of $\bar{l}$={2B, 6B, 8B, . . . } units from the LSB detector 385 so that when the LSB optical detector 385 is centered on a reflective line the corresponding ~LSB optical detector 383 is centered on a non-reflective line. The ~MSB optical detector 389 may be located a distance of $\bar{l}$={2B, 6B, 8B, . . . } units from the MSB optical detector 387 so that when the MSB optical detector 387 is centered on a reflective line the corresponding ~MSB optical detector 389 is centered on a non-reflective line. In one embodiment the distances l and $\bar{l}$ are minimized. As discussed above with respect to FIG. 16, each reflective line 495 has the same width $t_r$ and are evenly spaced from one another by a distance $t_s$ (for example, $t_s$=2B units wide). In one embodiment, the reflective line width and the non-reflective line width are equal (i.e., $t_r$=$t_s$). When the difference between the output voltage of the MSB optical detector 387 and the ~MSB optical detector 389 or the difference between the output voltage of LSB optical detector 385 and the ~LSB optical detector 383 is greater than a predetermined value, the respective optical detector may be assigned a logic value of 1. When the difference between the output voltage of the MSB optical detector 387 and the ~MSB optical detector 389 or the difference between the output voltage of the LSB optical detector 385 and the ~LSB optical detector 383 less than a predetermined value (i.e., a reflective line is not detected), the optical detector may be assigned a logic value of 0. As discussed above, the distance that the distal end of the flexible track 416 is moved away from or toward the cassette may be determined based on the transitions of the optical detectors between logic 1 and logic 0.

The signal to noise ratio may be increased by taking a difference between the output voltage of the MSB optical detector 387 and the output voltage of the ~MSB optical detector 389 and a difference between the LSB optical detector 385 and the output voltage of the ~LSB optical detector 383. In addition, the system is self-balancing because it is centered on the difference between a reflective line and a non-reflective line of the flexible track 316. This embodiment allows for compensation of offsets due to the optical assembly and to gradual irregularities in the surface of the flexible track 316.

Computer-executable instructions for determining the position of a flexible track according to the above-described method may be stored on a form of computer readable media. Computer readable media includes volatile and non-volatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital versatile disks (DVD) or other optical storage, magnetic cassettes, magnetic tape, magnetic disk storage or other magnetic storage devices, or any other medium which can be used to store the desired instructions and which may be accessed by system 10 (shown in FIG. 1), including by internet or other computer network form of access.

This written description used examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims. The order and sequence of any process or method steps may be varied or re-sequenced according to alternative embodiments.

Many other changes and modifications may be made to the present invention without departing from the spirit thereof. The scope of these and other changes will become apparent from the appended claims.

We claim:

1. A catheter procedure system comprising:
a base;
a robotic mechanism having a longitudinal axis and being movable relative to the base along the longitudinal axis; and
a controller,
the robotic mechanism comprising:
a robotic drive base including at least one drive mechanism;
a rigid guide fixed relative to the robotic mechanism;
a flexible track having a distal end and a proximal end, wherein at least a portion of the flexible track is disposed within the rigid guide; and
a position detector configured to determine the position of the distal end of the flexible track relative to the rigid guide,
wherein the controller is configured to:
move the robotic mechanism relative to the base in a first direction;
move the flexible track relative to the robotic mechanism in a second direction, and use the position of the distal end of the flexible track relative to the rigid guide from the position detector to control or limit movement of the robotic mechanism relative to the base.

2. A catheter procedure system according to claim 1, wherein the flexible track includes a plurality of reflective sections, and
wherein the position detector is configured to detect light reflected off of the reflective sections of the flexible track and to determine the position of the distal end of the flexible track relative to the rigid guide based on the detected reflected light.

3. A catheter procedure system according to claim 2, wherein optical detector is positioned beneath the flexible track and beneath an opening in the rigid guide.

4. A catheter procedure system according to claim 2, wherein the position detector comprises at least one optical detector.

5. A catheter procedure system according to claim 4, wherein the at least one optical detector comprises a light emitting diode (LED) and a photo diode.

6. A catheter procedure system according to claim 4, wherein the position detector further comprises a housing having at least one transparent section.

7. A catheter procedure system according to claim 6, wherein the at least one optical detector is configured to emit light that passes through the transparent section of the housing onto the flexible track and to detect light reflected off of the reflective sections of the flexible track.

8. A catheter procedure system according to claim 2, wherein the translation position detector comprises a first translational optical detector and a second translational optical detector.

9. A catheter procedure system according to claim 8, wherein the first optical detector and the second optical detector are located within the position detector to output a two-bit Gray Code.

10. A catheter procedure system comprising:
a base;
a robotic mechanism having a longitudinal axis and being movable relative to the base along the longitudinal axis; and
a controller,
the robotic mechanism comprising:
a robotic drive base including at least one drive mechanism;
a cassette operatively secured to the robotic drive base;
a flexible track having a distal end and a proximal end, wherein at least a portion of the flexible track is disposed within the cassette; and
a position detector configured to determine the position of the distal end of the flexible track relative to the cassette,
wherein the controller is configured to:
move the robotic mechanism relative to the base in a first direction;
move the flexible track relative to the robotic mechanism in a second direction, and
use the position of the distal end of the flexible track relative to the cassette from the position detector to control or limit movement of the robotic mechanism relative to the base.

11. A catheter procedure system according to claim 10; wherein the cassette includes a rigid guide fixed relative to the robotic mechanism, wherein at least a portion of the flexible track is disposed within the rigid guide.

12. A catheter procedure system according to claim 10, wherein the flexible track includes a plurality of reflective sections, and
wherein the position detector is configured to detect light reflected off of the reflective sections of the flexible track and to determine the position of the distal end of the flexible track relative to the rigid guide based on the detected reflected light.

13. A catheter procedure system according to claim 12, wherein optical detector is positioned beneath the flexible track and beneath an opening in the rigid guide.

14. A method, comprising:
moving a robotic mechanism relative to a base in a first direction, the robotic mechanism having a longitudinal axis and being movable relative to the base along the longitudinal axis, the robotic mechanism comprising:
a robotic drive base including at least one drive mechanism;
a cassette operatively secured to the robotic drive base;
a rigid guide fixed relative to the robotic mechanism;
a flexible track having a distal end and a proximal end, wherein at least a portion of the flexible track is disposed within the rigid guide; and
a position detector;
moving the flexible track relative to the robotic mechanism in a second direction opposite the first direction,
using the position detector to determine the position of the distal end of the flexible track relative to the rigid guide; and
controlling or limiting movement of the robotic mechanism relative to the base based on the position of the distal end of the flexible track relative to the rigid guide.

15. A method according to claim 14, wherein the flexible track includes a plurality of reflective sections, the method further comprising:
detecting, by the position detector, light reflected off of the reflective sections of the flexible track and to determine the position of the distal end of the flexible track relative to the rigid guide based on the detected reflected light.

16. A method according to claim 15, wherein optical detector is positioned beneath the flexible track and beneath an opening in the rigid guide.

17. A method according to claim 15, wherein the position detector comprises at least one optical detector.

18. A method according to claim 17, wherein the at least one optical detector comprises a light emitting diode (LED) and a photo diode.

19. A method according to claim 17, wherein the position detector further comprises a housing having at least one transparent section.

20. A method according to claim 19, wherein the at least one optical detector is configured to emit light that passes through the transparent section of the housing onto the flexible track and to detect light reflected off of the reflective sections of the flexible track.

* * * * *